(12) United States Patent
Friedman

(10) Patent No.: US 11,020,212 B2
(45) Date of Patent: Jun. 1, 2021

(54) VASCULAR FILTRATION DEVICE

(71) Applicant: W. L. Gore & Associates, Inc., Newark, DE (US)

(72) Inventor: Nathan L. Friedman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 92 days.

(21) Appl. No.: 16/207,357

(22) Filed: Dec. 3, 2018

(65) Prior Publication Data

US 2019/0099253 A1     Apr. 4, 2019

Related U.S. Application Data

(63) Continuation of application No. 14/201,551, filed on Mar. 7, 2014, now Pat. No. 10,143,545.

(Continued)

(51) Int. Cl.
*A61F 2/01* (2006.01)
*A61B 17/3207* (2006.01)
*A61F 2/95* (2013.01)

(52) U.S. Cl.
CPC .......... *A61F 2/013* (2013.01); *A61B 17/3207* (2013.01); *A61F 2/95* (2013.01); *A61F 2002/015* (2013.01); *A61F 2002/018* (2013.01); *A61F 2230/008* (2013.01); *A61F 2230/0078* (2013.01)

(58) Field of Classification Search
CPC ...... A61F 2/013; A61F 2/95; A61F 2002/015; A61F 2002/018; A61F 2230/0078; A61F 2230/008; A61F 2/01; A61F 2/0103; A61F 2/0105; A61F 2/0108; A61F 2/011; A61F 2/012; A61F 2/014; A61F 2002/016; A61B 17/3207

See application file for complete search history.

(56) References Cited

U.S. PATENT DOCUMENTS 5,848,964 A    12/1998  Shaun Lawrence
5,941,896 A     8/1999  Kerr
(Continued)

FOREIGN PATENT DOCUMENTS

EP     1524005 A1    4/2005
JP     2006204630    8/2006
(Continued)

OTHER PUBLICATIONS

International Search Report and Written Opinion for PCT/US2014/022372 dated Oct. 20, 2014, corresponding to U.S. Appl. No. 14/201,551, 6 pages.

*Primary Examiner* — Erich G Herbermann

(57) ABSTRACT

Vascular filtering devices and methods for their use are disclosed. In some embodiments, the vascular filtering devices include an elongate member having an unsupported membrane bag portion attached thereto. The membrane may be porous in some examples. Multiple elongate extensions may also extend from the membrane, and may extend along the elongate member, such as to a proximal region of the elongate member. The unsupported membrane bag portion may be configured to inflate or otherwise radially expand away from the elongate member as a result of blood flowing through the vessel within which the vascular filtering device is positioned.

24 Claims, 8 Drawing Sheets

Related U.S. Application Data

(60) Provisional application No. 61/798,289, filed on Mar. 15, 2013.

(56) References Cited

U.S. PATENT DOCUMENTS

| | | | |
|---|---|---|---|
| 6,142,987 A | 11/2000 | Tsugita | |
| 6,171,328 B1 | 1/2001 | Addis | |
| 6,245,088 B1 | 6/2001 | Lowery | |
| 6,361,545 B1 | 3/2002 | Macoviak | |
| 6,395,014 B1 * | 5/2002 | Macoviak | A61F 2/013 606/194 |
| 6,616,682 B2 | 3/2003 | Joergensen | |
| 6,652,554 B1 | 11/2003 | Wholey | |
| 7,174,636 B2 * | 2/2007 | Lowe | A61F 2/013 210/241 |
| 7,537,601 B2 * | 5/2009 | Cano | A61F 2/013 606/200 |
| 7,621,935 B2 | 11/2009 | Saito | |
| 7,706,861 B2 | 4/2010 | Windheuser | |
| 2002/0161395 A1 | 10/2002 | Douk | |
| 2003/0176884 A1 | 9/2003 | Berrada | |
| 2004/0002730 A1 * | 1/2004 | Denison | A61F 2/013 606/200 |
| 2004/0193208 A1 | 9/2004 | Talpade | |
| 2004/0220610 A1 * | 11/2004 | Kreidler | B32B 27/322 606/200 |
| 2007/0142858 A1 * | 6/2007 | Bates | A61F 2/013 606/200 |
| 2007/0233175 A1 | 10/2007 | Zaver | |
| 2008/0255606 A1 | 10/2008 | Mitra | |
| 2009/0138037 A1 * | 5/2009 | Griffin | A61F 2/013 606/200 |
| 2010/0191273 A1 | 7/2010 | Keating | |
| 2010/0262219 A1 * | 10/2010 | Frimerman | A61M 25/10 623/1.11 |
| 2012/0330346 A1 | 12/2012 | Frimerman | |

FOREIGN PATENT DOCUMENTS

| | | |
|---|---|---|
| WO | WO-2004039287 A2 | 5/2004 |
| WO | WO-2005042081 A1 | 5/2005 |
| WO | WO-2005070336 A1 | 8/2005 |
| WO | WO-2007061418 A2 | 5/2007 |
| WO | WO-2011144240 A1 | 11/2011 |
| WO | WO-2011151911 A1 | 12/2011 |

* cited by examiner

VASCULAR FILTRATION DEVICE

CROSS-REFERENCE TO RELATED APPLICATION

This application is a continuation of U.S. patent application Ser. No. 14/201,551, filed Mar. 7, 2014, which claims the benefit of U.S. Provisional Application 61/798,289, filed Mar. 15, 2013, both of which are incorporated herein by reference in their entireties for all purposes.

TECHNICAL FIELD

The present disclosure relates to deployable filtration devices, including filtration devices that may be deployed in a conduit within a patient, and to methods of making and using the devices.

BACKGROUND

Deployable filtration devices are useful for filtering bodily fluids that flow through conduits within the human body. One example of a deployable filtration device includes a wire frame covered by a sheet of filter material and secured to a distal end of a support wire. The device is delivered to a location in a blood vessel using a delivery catheter by advancing the delivery catheter through the blood vessel and advancing the device through a lumen of the delivery catheter and causing the device to exit the lumen of the catheter for placement within the blood vessel. The wire frame can often include a shape memory property, such that when the device exits the lumen of the catheter, the shape memory property of the wire frame causes the device to expand and assume a deployment configuration within the blood vessel. The filter material of the device prevents debris (e.g., embolic debris) that may be carried by blood flowing through the blood vessel from flowing downstream of the location and further into the vasculature.

During interventional vascular procedures (e.g., transcatheter or surgical vasculature procedures), embolic debris (e.g., thrombi, clots, plaques, etc.) may be liberated from their sources and may obstruct perfusion of vasculature located downstream of the sources. Such obstruction of vascular perfusion can result in cellular ischemia and/or cellular death. Deployable filtration protection may capture emboli liberated during an interventional procedure, and may thus reduce the risk of embolic complications (e.g., an embolic stroke) associated with interventional vascular procedures.

SUMMARY

In accordance with an embodiment, a vascular filtering device comprises an elongate member and a membranous member. The elongate member has one or more apertures in a wall of the elongate member and a lumen that extends from a proximal region of the elongate member and is in fluid communication with the one or more apertures. The membranous member comprises a bag portion and a plurality of elongate extensions of the bag portion. The bag portion comprises a porous membrane. A distal region of the bag portion is attached to a distal portion of the elongate member. In some embodiments each of the elongate extensions is integral with the bag portion and extends through an aperture of the one or more apertures and through the lumen of the elongate member, and exits the lumen at the proximal region of the elongate member.

In various embodiments, the plurality of elongate extensions and the bag portion may be formed from a single sheet of material. The plurality of elongate extensions and the bag portion may be formed from a sheet of ePTFE material. While in some embodiments the plurality of elongate extensions may comprise the porous membrane, in some embodiments the plurality of elongate extensions do not comprise the porous membrane. The elongate member may include a number of apertures in the wall of the elongate member equal to the number of elongate extensions of the plurality of elongate extensions, where each elongate extension passes through a separate aperture in the wall of the elongate member.

In some embodiments the elongate member comprises three apertures in the wall of the elongate member and the membranous member comprises three elongate extensions of the bag portion. The plurality of elongate extensions of the bag portion may extend from a proximal portion of the bag portion. The plurality of elongate extensions may be spaced approximately equidistantly about a perimeter of the proximal portion of the bag portion. An application of a proximally directed force to the plurality of elongate extensions may impart a distributed force about the perimeter of the proximal portion. The elongate member may comprise a shapeable tip portion. The shapeable tip portion may include a coil. The elongate member may be a tubular member, and the lumen may be a central lumen of the tubular member. The elongate member may be a tubular member, and the lumen may be defined within a wall of the tubular member. The tubular member may further include a central lumen that is different from the lumen defined within the wall of the tubular member. The elongate member may comprise a solid core. In some embodiments the lumen is defined by a groove in an exterior surface of the solid core. The vascular filtering device may further comprise one or more layers of material over the solid core, wherein the lumen may be defined by the one or more layers of material and the groove in the exterior surface of the solid core. The elongate member may comprise a guidewire. The elongate member may comprise a hypotube. An application of a proximally directed force to the plurality of elongate extensions may cause the bag portion to collapse against an external surface of the elongate member.

The vascular filtering device may further comprise, in accordance with an embodiment, a first stop member adapted to limit an amount of distal translation of an elongate extension of the plurality of elongate extensions of the bag portion. While in some embodiments the first stop member may be disposed proximal of the proximal region of the elongate member, in some embodiments the first stop member may be disposed distal of the proximal region of the elongate member and proximal of the one or more apertures in the wall of the elongate member. The first stop member may comprise a knot in at least one of the elongate extensions of the plurality of elongate extensions of the bag portion. The vascular filtering device may further comprise a second stop member adapted to limit an amount of proximal translation of an elongate extension of the plurality of elongate extensions of the bag portion.

The porous membrane may be adapted to permit blood to pass through the porous membrane when the vascular filtering device is deployed in a blood vessel of a patient, and may be adapted to prevent embolic debris from passing through the porous membrane. The vascular filtering device may further comprise one or more struts disposed in contact with a surface of the bag portion. The membranous member may further comprise one or more radiopaque markers. In some embodiments the vascular filtering device does not include a shape memory property.

In accordance with another embodiment, a vascular filtering device comprises an elongate member and a membranous member. The elongate member has a plurality of apertures in a wall of the elongate member and a lumen that extends from a proximal region of the elongate member and in fluid communication with the plurality of apertures. The membranous member comprises a bag portion and a plurality of elongate extensions of the bag portion. The bag portion comprises a porous membrane. A distal region of the bag portion is attached to a distal portion of the elongate member. In some embodiments each of the elongate extensions is integral with the bag portion and extend through an aperture of the plurality of apertures and through the lumen, and exits the lumen at the proximal region of the elongate member.

In accordance with another embodiment, a vascular filtering device comprises an elongate member and a membranous member. The elongate member has a plurality of apertures in a wall of the elongate member and a lumen that extends from a proximal region of the elongate member and in fluid communication with the plurality of apertures. The membranous member comprising a bag portion and a plurality of elongate extensions of the bag portion. The bag portion comprises a porous membrane. A distal region of the bag portion is attached to a distal portion of the elongate member. In some embodiments each of the elongate extensions is integral with the bag portion and extends through an aperture of the plurality of apertures and through the lumen, and exits the lumen at the proximal region of the elongate member. In some embodiments the vascular filtering device does not include a shape memory property.

In accordance with another embodiment, a vascular filtering device comprises an elongate member and a membranous member. The elongate member has one or more apertures in a wall of the elongate member and a lumen that extends from a proximal region of the elongate member and is in fluid communication with the one or more apertures. The membranous member comprises a bag portion and a plurality of tethers that extend from the bag portion. The bag portion comprises a porous membrane. A distal region of the bag portion is attached to a distal portion of the elongate member. In some embodiments each of the tethers extends through an aperture of the one or more apertures and through the lumen, and exits the lumen at the proximal region of the elongate member. In various embodiments, each tether of the plurality of tethers may be sutured to the bag portion.

In accordance with another embodiment, a vascular filtering device comprises a first elongate member, a second elongate member, and a membranous member. The first elongate member has one or more apertures in a wall of the first elongate member and a lumen that extends from a proximal region of the first elongate member and is in fluid communication with the one or more apertures. The membranous member comprises a bag portion and a plurality of elongate extensions of the bag portion. The second elongate member that includes a distal end that is attached to each elongate extension of the plurality of elongate extensions of the bag portion. The distal end of the second elongate member is disposed within the lumen of the first elongate member. A proximal end of the second elongate member extends proximal of the proximal region of the first elongate member. The bag portion comprises a porous membrane. A distal region of the bag portion is attached to a distal portion of the first elongate member. In some embodiments each of the elongate extensions is integral with the bag portion and extends through an aperture of the one or more apertures In accordance with another embodiment, an implantable filter comprises a filter element, a plurality of flexible tethers, and a means to maintain the distal end in a set orientation. The filter element has a closed distal end and an open proximal end. The plurality of flexible tethers is associated with the proximal end. The tethers are adapted to extend relative to the set orientation of the distal end so as to allow the filter element to open in response to flow of fluid through the filter element.

In accordance with an embodiment, a method of providing vascular filtration comprises: providing a vascular filtration device; applying a proximally directed force to the plurality of elongate extensions of the bag portion, wherein the application of the force causes the bag portion to collapse against the elongate member; advancing, while maintaining application of the force, the distal portion of the elongate member to a deployment site within a blood vessel; and ceasing application of the force, wherein blood flow through the blood vessel causes the bag portion to expand radially away from the tubular member. The vascular filtration device comprises: an elongate member having one or more apertures in a wall of the elongate member and a lumen that extends from a proximal region of the elongate member and in fluid communication with the one or more apertures; and a membranous member comprising a bag portion and a plurality of elongate extensions of the bag portion. The bag portion comprises a porous membrane. A distal region of the bag portion is attached to a distal portion of the elongate member. In some embodiments each of the elongate extensions is integral with the bag portion and extends through an aperture of the one or more apertures and through the lumen, and exits the lumen at the proximal region of the elongate member.

In accordance with another embodiment, the method of providing vascular filtration may further comprise advancing a treatment device through the lumen to a location upstream of the vascular filtration device, and using the treatment device to perform an interventional vascular procedure. The treatment device may be a thrombectomy device, and the interventional vascular procedure may be a thrombectomy procedure. The treatment device may be an atherectomy device, and the interventional vascular procedure may be an atherectomy procedure. The treatment device may be a stent, and the interventional vascular procedure may be a stenting procedure. The treatment device may be an angioplasty balloon, and the interventional vascular procedure may be an angioplasty procedure. The vascular filtration device and the treatment device may be each located within the blood vessel. The blood vessel may include first and second branch vessels, and the vascular filtration device may be deployed in the second branch vessel; and the method may further comprise advancing a treatment device through the lumen to a location in the first branch vessel and using the treatment device to perform an interventional vascular procedure. The method may further comprise aspirating debris collected by the vascular filtration device from the bag portion. In various embodiments of vascular filtering devices as provided herein, the vascular filtering device may not include a wire frame. In some embodiments, the implantable filter as provided herein may not include a wire frame.

In accordance with another embodiment, a vascular filtering device comprises an elongate member and a membranous member. The elongate member has one or more apertures in a wall of the elongate member, and a lumen that extends from a proximal region of the elongate member and in fluid communication with the one or more apertures. The membranous member comprises a bag portion and a plurality of elongate extensions of the bag portion. The bag portion comprises a membrane. A distal region of the bag portion is attached to a distal portion of the elongate member. In some embodiments each of the elongate extensions is integral with the bag portion and extends through an aperture of the one or more apertures and through the lumen of the elongate member, and exits the lumen at the proximal region of the elongate member.

In various embodiments, the vascular filtering device may be configured to act as a vessel occluder. The membrane may be substantially non-porous. The membrane may be substantially impermeable to blood. The vasculature filtering device may be configured to act as a temporary vessel occluder.

In accordance with another embodiment, a vascular filtering device comprises an elongate member and a membranous member. The elongate member has one or more apertures in a wall of a first distal region of the elongate member and a lumen that extends from a proximal region of the elongate member and is in fluid communication with the one or more apertures. The membranous member comprises a bag portion and a plurality of elongate extensions of the bag portion. The bag portion comprises a porous membrane, an attachment region and a mouth region. The attachment region of the bag is attached to a second distal portion of the elongate member and the mouth region is located distal to said attachment region. In some embodiments each of the elongate extensions is integral with the bag portion and extends through an aperture of the one or more apertures and through the lumen of the elongate member, and exits the lumen at the proximal region of the elongate member.

In various embodiments the vasculature filtering may be configured to be advanced retrograde in a blood circulation.

DETAILED DESCRIPTION

Figure 1A:
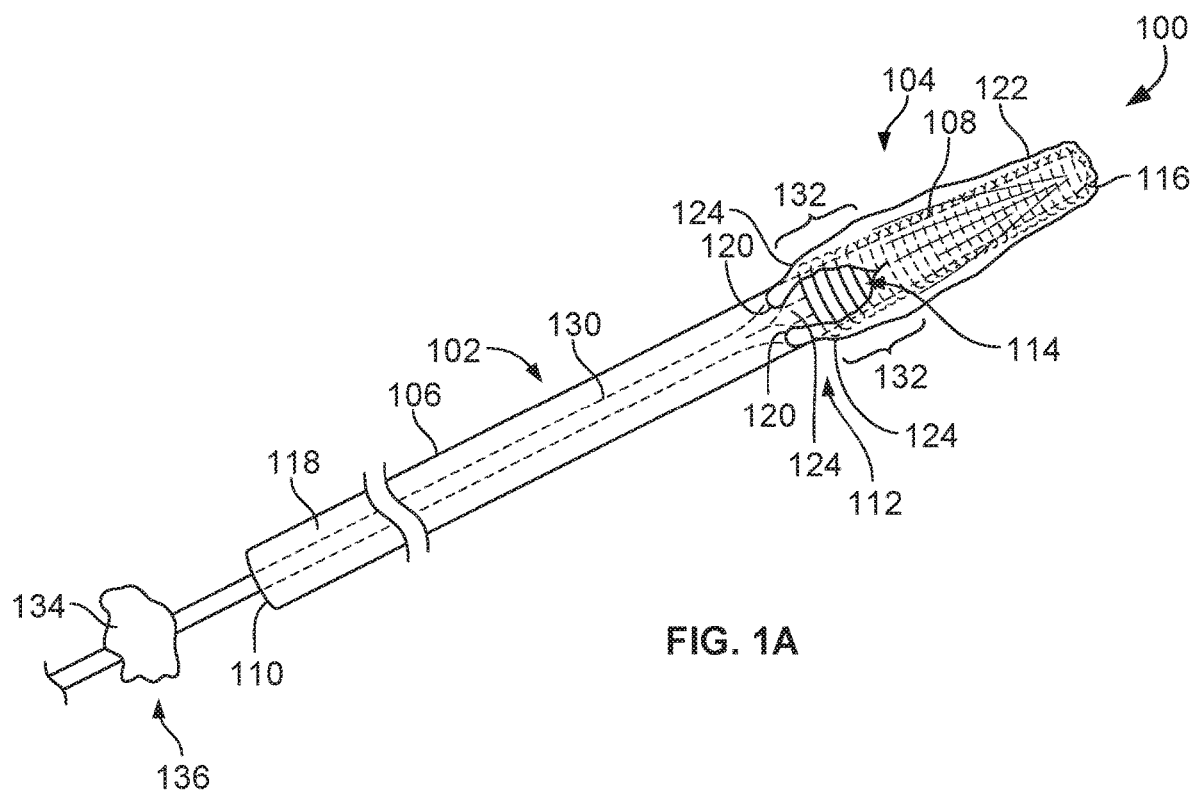
FIG. 1A is a perspective view of an embodiment of a filtration device in a delivery configuration.
Figure 1B:
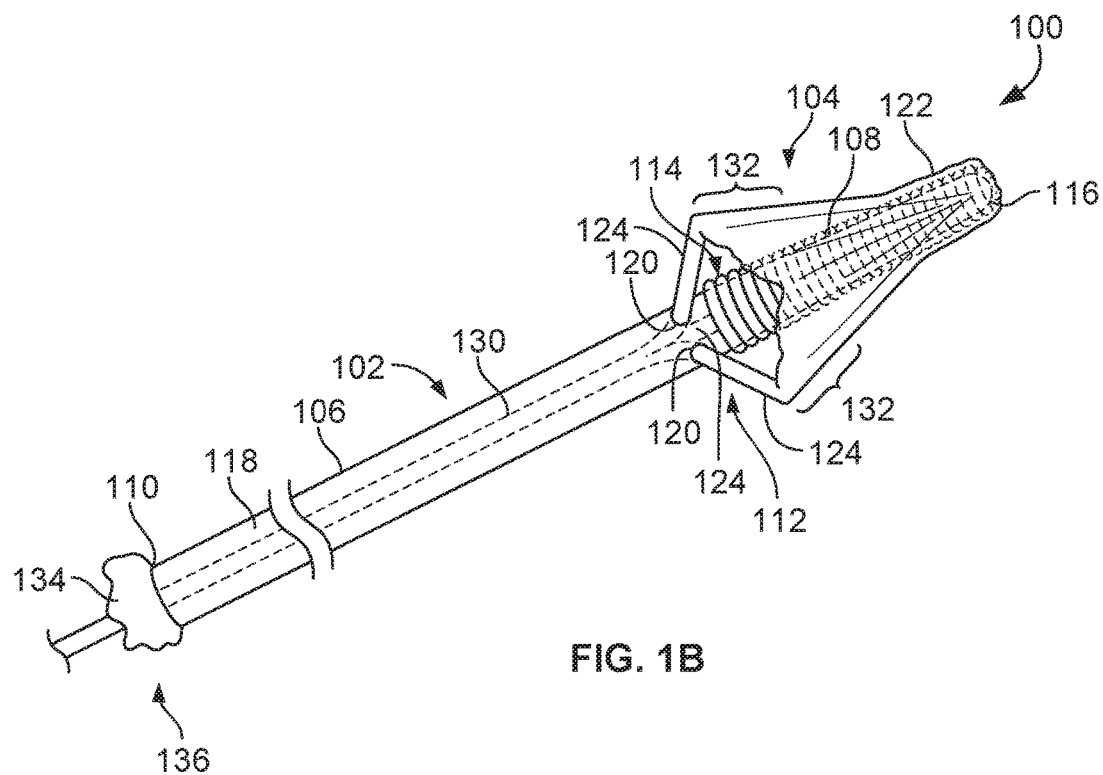
FIG. 1B is a perspective view of the embodiment of the filtration device of FIG. 1A in a deployed configuration.
Figure 1C:
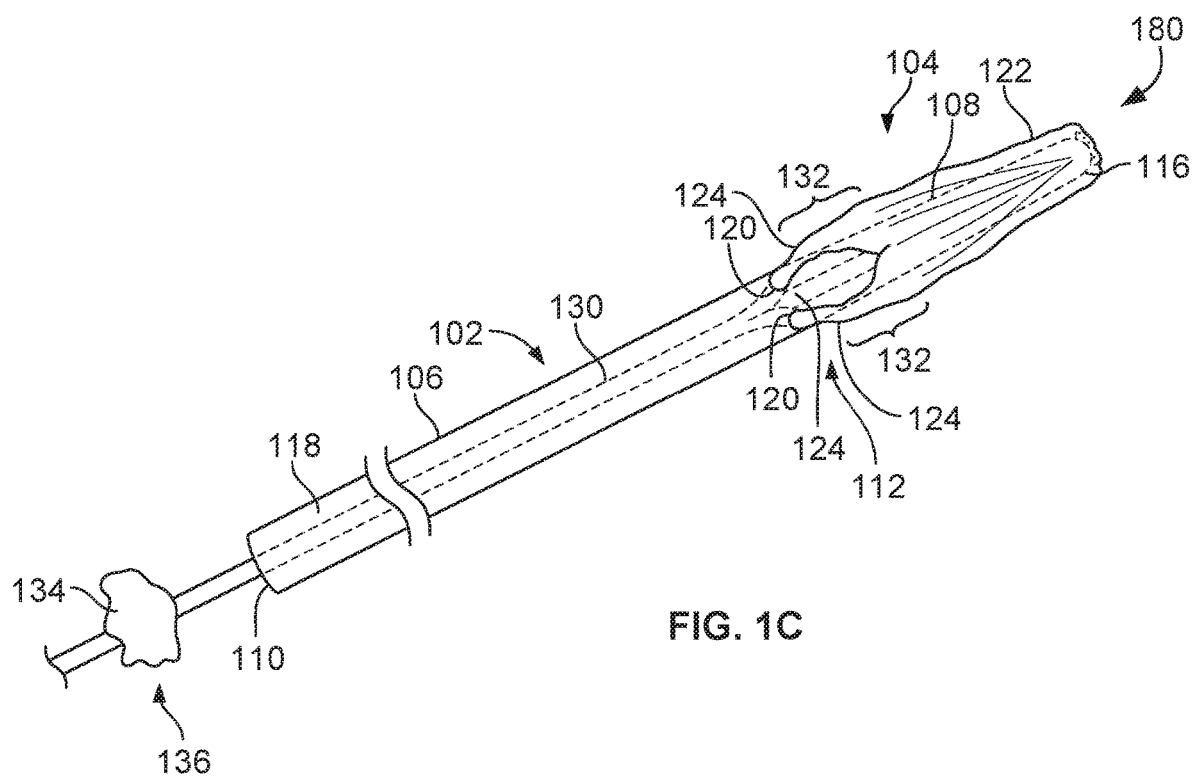
FIG. 1C is a perspective view of another embodiment of a filtration device in a delivery configuration.
Figure 1D:
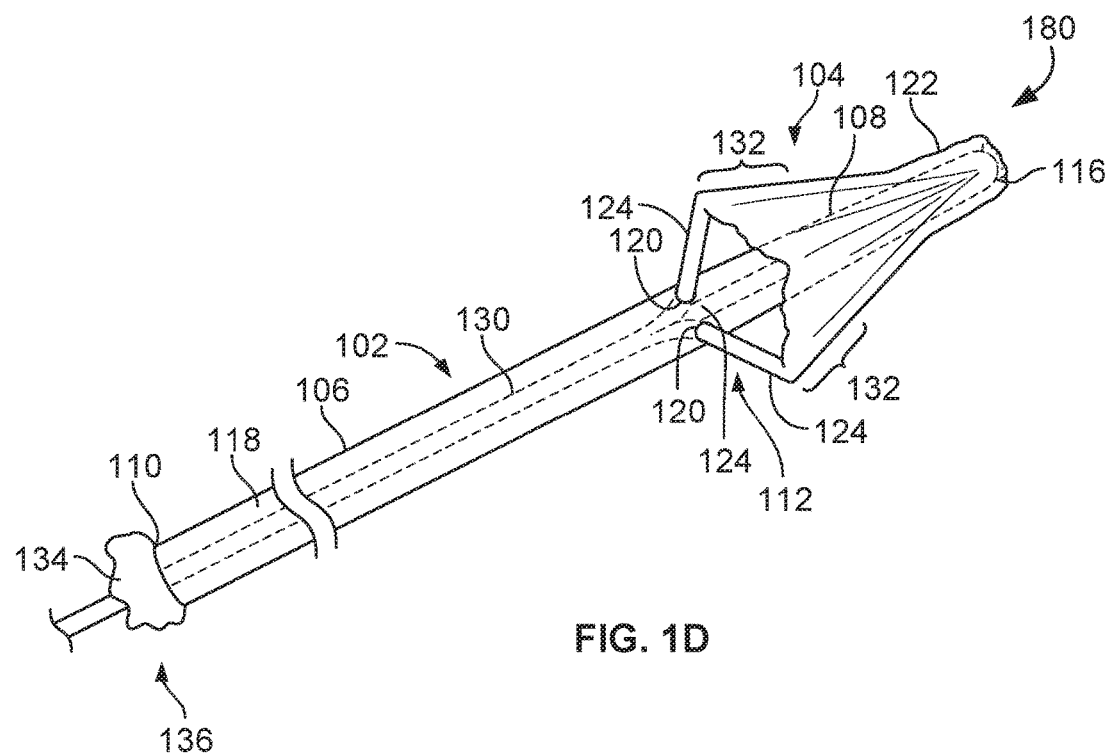
FIG. 1D is a perspective view of the embodiment of the filtration device of FIG. 1C in a deployed configuration.

FIGS. 1A and 1B illustrate an embodiment of a filtration device 100 that can be delivered to, and deployed in, a conduit such as an artery or vein, or generically, a blood vessel, within a patient. FIGS. 1C and 1D show another embodiment of a filtration device 180 that can be delivered to, and deployed in, a blood vessel. FIGS. 1A and 1C show the filtration devices 100, 180 in a delivery configuration, and FIGS. 1B and 1D show the filtration devices 100, 180 in a deployed configuration. For example, in some embodiments, the filtration device 100 or 180 can be used to filter blood or other fluid flowing through a blood vessel before, during, or after an interventional procedure, vascular procedure, or surgical procedure. In some embodiments, embolic debris or other debris may be displaced into the blood stream by a procedure or by preparation for the procedure, and the filtration device 100 or 180 may filter the blood or other fluid to prevent the debris from advancing beyond the deployed location of the filtration device. In some embodiments, the filtration device 100 or 180 may provide a distal filtration element integrated with a guidewire.

The terms "proximal" and "distal," as used herein in relation to a device or device component, refer respectively, to directions closer to the device's hub or operator (and farther away from the device's tip) and closer to the device's tip (and farther away from the device's hub or operator).

When deployed in a blood vessel, the filtration device 100 or 180 may permit blood to pass through the device for perfusion of the downstream vasculature, and may catch or trap particles having at least a predetermined size that are carried by the blood. In accordance with an embodiment, the filtration device 100 or 180 may trap emboli within the device, or within a volume defined by the device. In some embodiments, the emboli may be aspirated or otherwise removed from within the filtration device 100 or 180, or from within the volume defined by the device, while the filtration device 100 or 180 remains deployed within the blood vessel. In some embodiments, the filtration device 100 or 180, along with the captured emboli, may be removed from the blood vessel.

The filtration device 100 or 180 can be used to prevent material or debris from flowing downstream in the blood vessel and deeper into the patient's vasculature, while still permitting perfusion of the downstream tissue with blood that passes through the device. In some embodiments, filtration device 100 or 180 is configured to be advanced antegrade into the circulation and in some embodiments the filtration device 100 or 180 is configured to be advanced retrograde into the circulation.

As such, in addition to minimizing the risk of an embolic obstruction of a downstream vessel, downstream tissue may continue to be supplied with oxygen-carrying blood for a deployment location within an artery, so that cellular injury may be prevented or minimized. For deployment within a vein, for example, embolic debris may be captured without substantially disrupting circulation and return of blood to the heart.

In some embodiments, the filtration device 100 or 180 may filter blood flowing through a peripheral blood vessel, a cardiac blood vessel, a pulmonary blood vessel, an intracranial blood vessel, or another type of blood vessel. In various embodiments, the filtration device 100 or 180 may be used to filter blood in an artery or in a vein. Without limitation, embodiments of procedures during which the filtration device 100 or 180 may be used to provide distal filtration can include a thrombectomy procedure, including a mechanical thrombectomy procedure shortly after a patient has had an acute ischemic stroke, an atherectomy procedure, a stenting procedure, an angioplasty procedure, a coiling procedure, a deep vein thrombosis procedure, a lower limb ischemia procedure, a renal intervention (e.g., stenting, angioplasty, or coiling), a saphenous vein graft procedure, or other interventional, vascular, or surgical procedures. In some embodiments, such procedures may be used to treat conditions or defects such as clots, blockages, lesions, thrombi, plaque buildup, and others. For simplicity, reference to such embodiments of procedures will hereinafter be referred to, generically, as an "interventional vascular procedure."

In some embodiments, the filtration device 100 or 180 can be delivered to a delivery site within a blood vessel prior to initiation of an interventional vascular procedure, and can be deployed within the vessel. In some embodiments, the filtration device 100 or 180 can be delivered and deployed during an interventional vascular procedure. In a deployed configuration, for example, the filtration device 100 or 180 may adequately appose an inner surface of a wall of the blood vessel such that a portion of the filtration device (e.g., a rim or rim portion of the filtration device) substantially seals against or is urged against the wall of the blood vessel and substantially prevents passage of debris or material between the wall of the vessel and the filtration device 100 or 180 or portion of the device. The blood may enter an opening or mouth (e.g. mouth region) defined by the deployed filtration device 100 or 180 and may pass through filtration device 100 or 180, but the debris may be restricted from further downstream movement by the filtration device 100 or 180, and may be trapped in a region defined by the deployed filtration device. Accordingly, debris (e.g., embolic debris) or material that may be liberated during the interventional vascular procedure and carried by blood flowing through the blood vessel can be substantially prevented from flowing downstream of (e.g., distal of) the location of the deployed filtration device 100 or 180.

Following completion of the interventional vascular procedure, the filtration device 100 or 180 and any material or debris collected by the filtration device may be removed from the delivery site, as will be described in further detail below. In some embodiments, debris collected by the filtration device 100 or 180 may be aspirated (e.g., by an aspiration catheter) or otherwise removed from the delivery site prior to removal of the filtration device. For example, the debris or material can be removed from within the filtration device 100 or 180 or from within a volume or region defined by the device, where the debris or material may be trapped or collected by the device. The debris may be removed, for example, while the interventional vascular procedure is taking place or following the conclusion of the procedure. In this manner, the risk of complications (e.g., an embolic stroke or a pulmonary embolism) that could result from passage of such debris may be significantly reduced.

In some embodiments, deployment of the filtration device 100 or 180 may be assisted, at least in part, by fluid (e.g., blood) from the body's circulatory system flowing through the blood vessel. The fluid from the body's circulatory system may be flowing through the vessel based on the circulatory system's blood pressure, for example. The flow of blood through the vessel, in combination with an alteration of a tension associated with the filtration device 100 or 180, may encourage an expansion or transition generally in an outward radial direction (e.g., with reference to a support tube or support wire of the device) of at least a portion of the filtration device 100 or 180 within the vessel, and may cause the filtration device 100 or 180 to transition from the delivery configurations shown in FIGS. 1A and 1C, respectively, to the deployed configurations shown in FIGS. 1B and 1D. When the filtration device 100 or 180 deploys in this manner, a portion of the filtration device 100 or 180 may substantially seal or be urged against an inner wall surface of the vessel.

In some embodiments, deployment of the filtration device may occur based on the alteration of the tension associated with the filtration device 100 or 180 and the fluid flow through the vessel. In some embodiments, the filtration device 100 or 180 may not include a shape memory property, and deployment of the filtration device may not be aided by a shape memory property, for example. In some embodiments, the filtration device 100 or 180 may advantageously include a very low delivery profile, and may rely on fewer delivery components as compared to some traditional vessel filter devices. In accordance with an embodiment, delivery, deployment, and removal of filtration device 100 or 180 can be performed without using a delivery catheter or a delivery sheath, in some embodiments. This can simplify certain aspects of an interventional vascular procedure or a distal filtration procedure, as fewer delivery components may be used or exchanged before, during, or after the procedure, for example. Also, in some embodiments, the filtration devices described herein may permit distal filtration to be used in locations where access was previously too difficult, either because of the small size of the vessels or the tortuous nature of the vasculature. The filtration device 100 or 180 may not include certain structural components, such as a wire or metal frame, or a frame that includes a shape memory property, that are included on some traditional vessel filter devices.

In some embodiments, deployment of the filtration device 100 or 180 may not rely on an expansion of a wire frame or a metal frame, for example, and indeed, in some embodiments the filtration device 100 or 180 does not include a wire frame or a metal frame. In some embodiments, the filtration device 100 or 180 does not include a frame or support structure that has a shape memory property, for example.

In some embodiments, a fluid from outside of the body's circulatory system, such as saline, blood, or a blood substitute, may be injected into the blood vessel upstream of the filtration device 100 or 180. The injected fluid may supplement the circulatory system fluid (e.g., blood) flowing through the vessel, and may assist in deploying the filtration device 100 or 180. Injecting fluid to aid with deployment of the filtration device 100 or 180 may be advantageous when the device is deployed, for example, in a vessel where blood pressure is relatively low. While in some embodiments blood flow or blood pressure assist in deployment of the device, in some embodiments (e.g. in the neurovasculature) blood flow and blood pressure in combination assist in deployment of the filtration device 100 or 180.

The injected fluid may be stored in a bag, container, or delivery apparatus (e.g., a syringe) outside of the body of the patient prior to the injection of the injected fluid, for example. The injected fluid and circulatory system fluid flowing in the vessel may, in combination with an alteration of a tension associated with the filtration device 100 or 180, encourage an outward expansion or transition in a radial direction of at least a portion of the filtration device 100 or 180 within the vessel, and may cause the filtration device 100 or 180 to transition from the delivery configurations shown in FIGS. 1A and 1C to the deployed configurations shown, respectively, in FIGS. 1B and 1D. When the filtration device 100 or 180 deploys in this manner, a portion of the filtration device 100 or 180 may substantially seal or be urged against an inner wall surface of the vessel. In some embodiments, an injection of fluid can be provided both while the device is being deployed, and also while the device remains deployed in the vessel. In some embodiments, an injection of fluid can be provided while the device is being deployed, and then can be discontinued. In some embodiments, the injected fluid is not used, and the device deploys based on the circulatory system fluid flow and the alteration of the tension associated with the device.

In some embodiments, the filtration device 100 or 180 may be placed or maintained in a delivery configuration by applying a tension to a portion of the filtration device 100 or 180. As will be discussed in greater detail below, a portion of the filtration device 100 or 180 may extend to a proximal location outside of the body of the patient, where the portion may be manipulated by a clinical operator. For example, the clinical operator may apply a tension (e.g., as by applying a proximally directed force) to the portion of the filtration device 100 or 180 that extends to the proximal location to place or maintain the filtration device 100 or 180 in a delivery configuration, whereby the applied tension may cause a distal portion of the filtration device (e.g., a filtration surface of the device) to be positioned against (e.g., pulled tightly against) an exterior surface of a delivery tube or other delivery element.

In this manner, the distal portion of the filtration device 100 or 180, including the portion of the filtration device that traps debris following deployment, may be located exterior of a delivery tube, guidewire, or other delivery element when the filtration device is maintained in the delivery configuration. Because the applied tension to a portion of the device maintains the distal portion of the device in the delivery configuration, in some embodiments the filtration device 100 or 180 may not be located within a lumen of a delivery catheter or sheath while the filtration device is delivered to the delivery site. In accordance with an embodiment, an exterior surface of the filtration device 100 or 180 may be generally exposed within the blood vessel (e.g., generally in full contact with blood flowing through the vessel) while the filtration device is being delivered to the delivery site, including as the device approaches the delivery site and just prior to deployment of the filtration device at the delivery site. In some embodiments, there may be no elements of the delivery system located between an external surface of the filtration device 100 or 180 and an inner wall of the blood vessel while the filtration device is maintained in the delivery configuration and delivered to the delivery site.

In some embodiments, the filtration device 100 or 180 may be delivered to the delivery site within the blood vessel without using a delivery catheter or sheath. In some embodiments, a delivery tube, on which a portion of the filtration device 100 or 180 is mounted, may pass through a lumen of a delivery catheter or sheath during an initial portion of the delivery, and may exit the lumen during a later portion of the delivery, for example during an approach to the delivery site. As will be explained in more detail below, in some embodiments the filtration device 100 or 180 may be used together with an adjunct therapeutic device (e.g., a suction catheter, a drug delivery catheter, a balloon therapy device, a cutting element, or the like) before, during, or after an interventional vascular procedure to implement filtration at a location downstream or distal of the procedure without having to exchange a catheter, for example.

As shown in FIGS. 1A, 1B, 1C, and 1D, the embodiment of the filtration device 100 or 180 includes an elongate member 102 and a membranous member 104. In some embodiments, a portion of the membranous member 104 is secured to a portion of the elongate member 102. In some embodiments, the elongate member 102 includes a tube 106, and a tip 108 that extends distally from the tube 106 to form a distal end portion of the elongate member 102. The tube 106 includes a proximal end 110, and the tip 108 includes a distal end 116.

In some embodiments, the tip 108 or a portion of the tip is an integral or unibody extension of the tube 106. In accordance with an embodiment, the tip 108 and the tube 106 can be formed from the same sheet or tube of material. The tip 108 of the filtration device 180, shown in FIGS. 1C and 1D, is an integral extension of the tube 106. A portion of the tip 108 of the filtration device 100, shown in FIGS. 1A and 1B, is also an integral extension of the tube 106. The tip 108 of the filtration device 100 also includes a coil 114. In some embodiments, the coil 114 is wrapped around the tip 108, as shown in FIGS. 1A and 1B. In some embodiments, the tip 108 may be attached to the tube 106. Some embodiments do not include a coil 114, such as filtration device 180 shown in FIGS. 1C and 1D.

In some embodiments, an outer diameter of the tip 108 or a portion of the tip may taper to a smaller outer diameter near its distal end 116. Such tapering may occur along the entire length of the tip 108, in an embodiment, or along only a distal portion of the tip 108, in various embodiments. In some embodiments, the tip 108 may have an outer diameter that is the same or about the same as the outer diameter of the tube 106. In some embodiments, the tip 108 may widen to a larger outer diameter near its distal end 116. Such widening may occur along the entire length of the tip 108, in an embodiment, or along only a distal portion of the tip 108, in various embodiments. Some embodiments do not include a tip 108.

FIGS. 1A and 1B show the distal end 116 of the tip 108 extending to near the end of the coil 114. In some embodiments, the distal end 116 of the tip 108 extends only to about the midpoint of the coil 114, or to a particular position along the length of the coil 114 (e.g., to a position about 10%, 20%, 25%, 30%, 40%, 60%, 70%, 75%, 80% or 90% of the length of the coil 114).

In some embodiments, the tip 108 of the filtration device 100 or 180 extends a particular distance distally beyond the distal portion of the bag 122. In accordance with embodiments, the tip 108 may extend about 5 mm, 10 mm, 20 mm, 30 mm, 40 mm, 50 mm, or more beyond the distal portion of the bag 122, in some embodiments. Similarly, in some embodiments the coil 114 may extend a particular distance (e.g., about 5 mm, 10 mm, 20 mm, 30 mm, 40 mm, 50 mm or more) distally beyond the distal portion of the bag 122.

In some embodiments, the distal end 116 of the tip 108 may be have a rounded shape that facilitates substantially atraumatic delivery of the filtration device to the delivery site, or that minimizes trauma to a surrounding vessel wall during delivery of the filtration device. In some embodiments, the tip 108 or a portion of the tip may be shapeable (e.g., bendable) such that an operator can optimally shape the tip 108 to a form that minimizes trauma to the surrounding vessel wall during delivery of the filtration device 100 to the delivery site. In accordance with an embodiment, the coil 114 may be shapeable.

The tube 106 of the elongate member 102 defines a lumen 118 that extends along a length of the tube 106. The tube 106 further defines one or more apertures 120 in a sidewall of the tube 106. In some embodiments, the apertures 120 may be positioned near a transition region 112 where the tube 106 and the tip 108 meet. Embodiments of the filtration device 100 and 180 shown in FIGS. 1A, 1B, 1C and 1D include three apertures 120, although only two apertures are visible in the figures. In other embodiments, the tube 106 may define more or fewer apertures 120 (e.g., one, two, four, five, six, seven, eight, or more). In some embodiments, the apertures 120 may be positioned on the tip 108, rather than on the tube 106.

In some embodiments, the apertures 120 may be spaced approximately equidistantly from one another about a circumference of the tube 106. In some embodiments, the apertures 120 may not be spaced equidistantly or may be unequally spaced from one another about the circumference of the tube 106. In some embodiments, the apertures 120 may be located about 10 mm to about 50 mm from the distal end 116 of the tip 108 of the elongate member 102. In some embodiments, the apertures 120 may have a circular shape and may have a diameter of about 0.004 inches to about 0.020 inches. In some embodiments, the apertures may be aligned circumferentially around the elongate member, and in other embodiments, the apertures may be offset or staggered along the length. In some embodiments a subset of the apertures is a first distance from the tip while a second subset of apertures is a second distance from the tip. In some embodiments, the filtration device may include an elongate member having a tube that defines apertures that include a non-circular shape (e.g., square, oval, rectangle, diamond, triangle, or others). In general, the apertures 120 may be sized to allow coupling of the elongate member 102 to the membranous member 104, as will be discussed in more detail below. In some embodiments, a portion of the coil 114 may extend proximally beyond the apertures 120. In some embodiments a proximal portion of the coil 114 may overlap a distal portion of the tube 106.

In some embodiments, the elongate member 102 comprises a guide wire that is adapted to be inserted through a blood vessel. In some embodiments, the elongate member 102 comprises a delivery tube. In a general embodiment, dimensions of the elongate member 102 may be selected according to a size of a particular conduit within which the filtration device 100 or 180 will be deployed. In accordance with an embodiment, a 0.010" guide wire or a 0.014" guide wire may be appropriate for use during neurovascular or intracranial procedures or applications. In some embodiments a 0.035" guide wire may be appropriate for use during cardiovascular, peripheral vascular, or other types of vascular procedures or applications. In some embodiments, the elongate member 102 may be sized such that the filtration device 100 or 180 can be used during procedures performed in significantly larger vessels (e.g., the great arch) during, for example, heart valve or aortic device procedures. In some embodiments, the elongate member 102 (e.g., a guide wire) may allow for delivery of an adjunct or therapeutic device, such as an angioplasty balloon, atherectomy device, cutting balloon, stent, suction device, drug delivery device, or others, along the elongate member 102.

In some embodiments, the tube 106 of the elongate member 102 may include one or more additional lumens that can allow for delivery, for example, of injected fluid from outside the body of the patient for embodiments that include an injection of fluid to aid in deployment of the filtration device 100 or 180. The one or more additional lumens may be used to carry the injected fluid to a location upstream of the filtration device, for example, where the fluid may exit the lumen at one or more openings (not shown) in the wall of the tube 106. In some embodiments, the injected fluid can include a therapeutic substance, such as an anti-clotting agent (e.g., heparain). In some embodiments, one or more adjunct or therapeutic devices may be passed through the lumen 118 (or through the one or more additional lumens, if appropriate) of the elongate member 102 during use of the filtration device.

The components of the elongate member 102 can be formed of one or more of a variety of biocompatible materials. In some embodiments, the tube 106, the tip 108, or both can be formed of nitinol (NiTi), stainless steel, L605 steel, a polymer material (e.g. a polyether block amide (PEBAX), polyimide, nylon, and PTFE), or any other appropriate biocompatible material. In some embodiments, the tube 106, the tip 108 or both can be cut (e.g., laser cut) from a hypotube. The hypotube may be cut, for example, to include a guidewire-flex profile. In some embodiments, the apertures 120 may be laser cut into the sidewall of the tube 106. As described above, in some embodiments the tip 108 may be an extension of the tube 106 (e.g., the tip 108 may comprise the distal portion of the tube 106), and may be formed from the same material as the tube 106. In some embodiments, the tip 108 may be attached to the tube 106, and the distal end of the tube 106 may be coupled to the proximal end of the tip 108 using standard techniques that will be known to those skilled in the art. In some embodiments, the tube 106, the tip 108, or both can be coated (e.g., dip coated) with an anti-clotting coating (e.g., heparin), or with a hydrophilic lubricious coating, or with a hydrophobic lubricious coating. Exemplary lubricious coatings include, without limitation, silicone-based and polyurethane based lubricious coatings.

Still referring to FIGS. 1A, 1B, 1C and 1D, the membranous member 104 includes a bag 122 and one or more tethers 124 that extend proximally from the bag 122. In the depicted embodiments, the membranous member 104 includes three tethers 124, although only two are visible in the figures. In some embodiments, the filtration device may include a membranous member that has a different number (e.g., one, two, four, five, six, seven, eight, or more) of tethers 124. In some embodiments, the number of tethers 124 may be equal to the number of apertures 120 in the tube 106. In some embodiments, apposition of the bag 122 against an inner wall of a blood vessel or other conduit 138, as shown in FIG. 2B, may increase as a number of tethers increases.

A distal portion of the bag 122 is attached to an area of the tip 108 of the elongate member 102. In the embodiments shown in FIGS. 1A, 1B, 1C, and 1D, the bag 122 is attached near the distal end 116 of the tip 108. The distal portion of the bag 122 may be attached to the tip 108 (or generally to the elongate member 102) by an adhesive, for example, or by other attachment methods that will be known to those of skill in the art. In some embodiments, the distal portion of the bag 122 is attached to the elongate member 102 with a fluorinated ethylene propylene (FEP) adhesive material, cyanoacrylate, or by melting the outer layer of the tube to serve as an adhesive or weld. In some embodiments, the distal portion of the tip 108 extends distally beyond the distal portion of the bag 122, and the bag 122 is attached to the tip 108 at a predetermined distance from the distal end 116.

In a deployed configuration of the filtration device 100 or 180, as shown in see FIGS. 1B and 1D, the bag 122 provides a filtration surface, and blood that flows beyond or downstream of the deployed location of the filtration device 100 or 180 passes through the filtration surface of the bag 122. In some embodiments, the bag 122 includes pores (not shown) that are sized to allow passage of blood (including blood components e.g., blood cells and platelets) and prevent passage of debris (e.g., embolic debris) or material carried by blood flowing through the bag 122. In some embodiments, the pores of the bag 122 may have a diameter in the range of about 30 microns (30 um) to 120 microns (um), and in some embodiments about 110 microns, so that debris, material, or particles carried by the blood and exceeding this predetermined size will be prevented from passing through the pores of the bag 122. In some embodiments, the bag 122 includes a porous membrane. In some embodiments, the bag 122 includes a micro-porous membrane. In some embodiments, the bag is non-porous and allows neither the passage of blood nor the passage of debris. In some such embodiments the device acts as a vessel occluder and can prevent the passage of blood or debris through the bag.

In some embodiments, the tethers 124 (or a portion of the tethers) also include pores (not shown), as described above with reference to the bag 122. In some embodiments, the tethers 124 do not include pores. In some embodiments, the tethers 124 include a porous membrane. In some embodiments, the tethers 124 include a micro-porous membrane.

The bag 122 may have various shapes. In some embodiments, the bag 122 may have a generally conical shape when deployed. In some implementations, the bag 122 may have a generally basket shape when deployed. In some embodiments, the bag 122 may have a generally umbrella shape when deployed. In some implementations, the bag 122 may have a generally sock shape or windsock shape when deployed. A cross-section of the bag 122 (or of a portion of the bag) have may a substantially circular shape. When deployed, the bag 122 may generally conform to the shape of the vessel wall.

In some embodiments, a rim or rim portion of the bag is adapted to appose the blood vessel wall in the deployed configuration so that any blood or material that passes beyond the deployed location must pass through the filtration surface of the bag (e.g., through the pores of the bag). The rim or rim portion of the bag may have a generally circular cross-section shape, and may effectively seal or be urged against a wall of a blood vessel or other conduit having a generally circular cross-section shape. A base area or proximal portion of the bag can generally define the rim of the bag and can define an opening or mouth of the bag, into which blood (and material carried by the blood) can flow.

In some embodiments, the filtration device 100 or 180 is configured to be used in a retrograde manner, i.e. the device is delivered to a target site in a direction opposite to that of blood flow. In some embodiments, a device configuration for retrograde use includes a reverse of the relative positions of one or more device components. In some embodiments, the opening or mouth of the bag and the one or more tethers are distal to the one or more points at which the bag is attached to the elongate member. In some such embodiments, a diameter of the bag tapers from a first diameter at a distal portion of the bag (near the opening or mouth of the bag) to a relatively smaller diameter at a proximal portion of the bag (e.g., where the bag is attached to the elongate member). In some embodiments, the bag 122 or a portion of the bag may include a tapered section. For example, when in a deployed configuration, the bag 122 may have a generally conical shape, where the bag has a generally circular cross-sectional shape, and where a diameter of the bag tapers from a relatively larger diameter at a proximal portion of the bag (near the opening or mouth of the bag) to a relatively smaller diameter at a distal portion of the bag (e.g., where the bag is attached to tip 108).

The bag 122 defines an interior of the device or a volume of the device, when deployed, where embolic debris or other material may be trapped or collected. As described above, a distal portion of the bag 122 may be fixedly attached to an area of the tip 108 near the distal end 116 of the tip 108 of the elongate member 102. The interior of the device or interior volume of the device may be defined at the proximal end by the mouth of the bag, at the distal end by the portion of the bag attached to the tip 108, and between the proximal and distal ends by the filtration surface of the bag.

In some embodiments, a shape of the filtration surface may aid in providing an apposition force against an inner surface of a wall of a blood vessel or other conduit in which the filtration device 100 is deployed. For example, as blood or other fluid flows through a bag 122 that has a tapered shape, force imparted on the tapered surface of the bag 122 may encourage or urge a portion of the bag (e.g., a rim portion of the bag) against the vessel wall. In some embodiments, fluid flowing through the tapered filtration surface may tend to exert an outward radial force on an inner side of the filtration surface, thereby forcing the proximal end region of the bag 122 against the inner surface of the wall of the vessel and thus helping to maintain the filtration device 100 at a desired position within the vessel. In some embodiments, the bag may have a non-tapered shape.

In some embodiments, the bag 122 may have a length of 10 mm to about 100 mm, and, in some embodiments, from about 10 mm to about 50 mm. In some embodiments, the length of the bag 122 may depend on the length of the tip 108 of the elongate member 102. In some embodiments, the length of the tip 108 is selected based on the length of the bag 122. In some embodiments, a diameter of the bag 122 or of a widest deployed portion of the bag (e.g., the rim portion of the bag) may be sized according to an inner diameter of a blood vessel or other conduit in which the filtration device 100 or 180 will be deployed.

In some embodiments, the one or more tethers 124 of the membranous member 104 respectively individually pass through the one or more apertures 120 in the tube 106. In some embodiments, the tethers 124 may be spaced (e.g., equidistantly from one another or unequally) about a circumference of the bag 122 to coincide with the spacing of the apertures 120 about the circumference of the tube 106 of the elongate member 102. In accordance with an embodiment, a distal portion of the bag 122 may be attached to the elongate member 102 in a manner that aligns the one or more tethers 124 with the one or more apertures 120. In some embodiments, two or more tethers pass through a single aperture. In an embodiment with six tethers, tether one and tether two may pass through a first aperture, tether three and tether four may pass through a second aperture, and tether five and tether six may pass through a third aperture.

In some embodiments, the one or more tethers 124 extend through the lumen 118 of the tube 106, and exit the tube 106 at or near the proximal end 110 of the tube, where the one or more tethers 124 may be manipulated by a clinical operator. In some embodiments, the tethers 124 can exit the lumen 118 through the proximal end of the tube. In some embodiments, the tethers 124 can exit the lumen 118 via one or more apertures in a sidewall of the tube 106 near the proximal end 110 of the tube 106.

In some embodiments, the tethers 124 may collectively form a tether bundle 130 inside the lumen 118. In some embodiments the tethers 124 collectively form a tether bundle 130 at the proximal end of the tube 106. In accordance with an embodiment, the tethers 124 may be twisted or rolled over a portion of the overall tether length to form the tether bundle 130. The tether bundle 130 may extend out of the proximal end 110 of the tube 106, or in some embodiments out of one or more openings in a side wall of the tube 106 near the proximal end 110 of the tube 106. In some embodiments, one or more tethers 124 or the tether bundle 130 are attached to a member (e.g. a ring or other securing structure) external to the tube 106 and adjacent to the one or more openings in a side wall of the tube 106 near the proximal end 110 of the tube 106. In some embodiments, the one or more tethers 124 or the tether bundle 130 exit the tube 106 external to the patient's body. In some embodiments the one or more tethers 124 or the tether bundle is attached to a wire in the lumen, thus allowing distal pushing (for antegrade applications) or proximal pulling (for retrograde applications) of the wire to aid in deployment.

As described above, a tension may be applied, as by a clinical operator or by a machine component, to the one or more tethers 124 or to the tether bundle 130, or to the member external to the tube 106, by providing a proximally directed force, which may cause the bag 122 to be collapsed against the elongate member 102 (e.g., against the tip 108 of the elongate member 102). In accordance with an embodiment, an inner surface of the bag 122 may be pulled against an outer surface of the elongate member 102 (e.g., against an outer surface of the tip 108) when a tension is applied to the one or more tethers 124 or tether bundle 130. By application of the tension to the one or more tethers 124 or tether bundle 130, the filtration device 100 or 180 may be placed or maintained in a delivery configuration or collapsed configuration, for example. The filtration device 100 or 180 may have a very low profile when the device is maintained in the delivery configuration, which may be advantageous for traversing a tortuous vasculature or very small blood vessels, in some embodiments. For example, with the low delivery profile and available delivery techniques without using an outer catheter or sheath, the filtration devices described herein may permit distal filtration to be used for applications or in locations where access was previously too difficult, either because of the small size of the vessels or the tortuous nature of the vasculature.

When the application of the tension to the one or more tethers 124 or tether bundle 130 is discontinued, a resulting slack in the one or more tethers 124 may permit the bag 122 or one or more portions of the bag 122 to move in a generally radially outward direction with respect to the elongate member 102. In some embodiments, the bag 122 or a portion of the bag 122 may move slightly distally as well. This may permit the filtration device 100 or 180 to assume the deployed configuration shown in FIGS. 1B and 1D, for example, in conjunction with an urging of the bag 122 or a portion of the bag 122 (e.g., the rim or a rim portion) against an inner wall of a blood vessel, as aided by a flow of fluid through the blood vessel. In some embodiments, the flow of fluid through the blood vessel is blood flowing as a result of the body's circulatory system. In some embodiments, the flow of fluid through the blood vessel is a fluid from outside of the body's circulatory system, such as saline, blood, or a blood substitute, that may be injected into the blood vessel. In some embodiments, the flow of fluid through the blood vessel is a combination of blood flowing as a result of the body's circulatory system and an injected fluid from outside of the body's circulatory system.

In some embodiments, each tether 124 includes, or extends from, a transitional region 132 of the bag 122. Generally, the transition regions 132 of the bag are disposed between the tethers 124 and the main body of the bag 122. The transitional region 132 has a shape and a length that may affect the degree to which the bag 122 may appose a wall of a blood vessel or other conduit. For example, as a length of the transitional region 132 decreases, the bag 122 may be able to better appose the wall of the blood vessel or other conduit. In some embodiments, the transitional regions 132 may have a length of about 1 mm to about 10 mm. In the embodiment of the filtration device 100 or 180, the transitional regions 132 have a triangular shape. However, in some embodiments, the transitional regions have other shapes (e.g., a pentagonal). In some embodiments, the transitional region 132 is not included, and the tethers 124 extend from the rim of the bag 122. In some embodiments, a length of the tether portion between the transition region 132 and the aperture 120 (that is, the portion of the tether 124 beyond the aperture 120), when in a deployed configuration, may be about twice a diameter of a blood vessel or other conduit in which the filtration device 100 or 180 is deployed.

In some embodiments, the filtration device 100 or 180 may assume various configurations. In accordance with an embodiment, the tethers 124 may be translatable along the length of the tube 106 of the elongate member 102, which may facilitate the filtration device assuming a delivery configuration or a deployed configuration. Referring particularly to FIGS. 1A and 1C, a tension may be applied to the tether bundle 130 (e.g., the tether bundle 130 may be pulled taut proximally by the operator) such that the tethers 124 are pulled proximally through the apertures 120 of the elongate member 102, causing the bag 122 to collapse against an outer surface of the tip 108 of the elongate member 102. In this manner, the filtration device 100 or 180 can assume a low profile delivery configuration, and can be delivered to the delivery site without using a delivery catheter that may otherwise be needed to collapse a filtration device that includes an underlying frame. In the delivery configuration, the tethers 124 may be taut, and the bag 122 may be collapsed against the tip 108 of the elongate member (e.g., against the coil 114 of the tip 108 in FIG. 1A, or against the tip 108 in FIG. 1C). In addition to being initially delivered to a site while in the delivery configuration, the device may also be repositioned within, or retracted from, the blood vessel after deployment by again tensioning the tether bundle 130 to place the device in the delivery configuration, and then repositioning or retracting as desired.

Referring particularly to FIGS. 1B and 1D, the tether bundle 130 may be released from a taut position to allow the tethers 124 to move distally through the apertures 120. As fluid flows between the bag 122 and the elongate member 102, the fluid exerts a force on the bag 122, causing the filtration surface of the bag 122 to extend radially from the outer surface of the tip 108, until the filtration device 100 assumes the deployed configuration. Thus, deployment of the filtration device 100 or 180 may not rely on expansion of a frame, or on a shape memory property of a frame. In the deployed configuration, the filtration device 100 or 180 may be operable to filter embolic debris and other debris or material carried by blood flowing through the blood vessel or other conduit.

The various components of the membranous member 104 can be formed of one or more of a variety of biocompatible materials. In accordance with an embodiment, the bag 122 and the tethers 124 may be formed of a polymeric material. Example materials that can be used to for the bag 122 and tethers 124 can include polytetrafluoroethylene (PTFE), expanded PTFE (ePTFE), silicone, polyester, or an elastomeric fluoropolymer, such as described in one or more of U.S. Pat. Nos. 7,049,380, 7,462,675, and 8,048,440, each of the contents of which are incorporated by reference herein for all purposes. In some embodiments, the bag 122 and the tethers 124 may be formed from a single sheet of material, which may provide for an easy manufacturing process for the membranous member 104 that does not include attaching the tethers 124 to the bag 122. In accordance with an embodiment, the single sheet of material may be cut to provide slits that extend from an edge of the sheet to a position in the sheet that marks the proximal end of the bag 122. In some embodiments, the material between the slits may then be twisted about themselves and heat-treated (e.g., using a heated die) to provide individual fibers that form the tethers 124. The tethers 124 may extend directly from the portion of the sheet that forms the bag 122 in an integral and unibody manner. In some embodiments, the single sheet is wrapped around a mandrel and heat treated to create a tube which is then slit, twisted and heated into struts.

In some embodiments, the bag 122 and the tethers 124 may alternatively be formed from separate materials and subsequently attached to one another. In accordance with an embodiment, the bag 122 may be a PTFE or ePTFE member and the tethers 124 may be polyester elongate members that are sutured to the bag 122.

Still referring to FIGS. 1A, 1B, 1C and 1D, in some embodiments, the filtration device 100 or 180 may include a stop member 134 that is adapted to prevent the tethers 124 from moving distally beyond a prescribed position along the length of the elongate member 102. In some embodiments, the stop member 134 may be disposed along a proximal end region 136 of the tether bundle 130. In the depicted embodiments, the stop member 134 is adapted to not pass distally of the proximal end 110 of the tube 106. In some embodiments, the stop member 134 and the tube 106 may provide a limit on a distance that the proximal end of the bag 122 may move in the distal direction. In accordance with an embodiment, a distance between the stop member 134 and the proximal end 110 of the tube 106 when the tether bundle 130 is pulled taut may provide an upper limit on how far the tethers 124 may move when tension on the tether bundle 130 is released. This limit may prevent the bag 122 from everting during deployment, for example. In various embodiments, based on the location of the stop member 134, the bag may be prevented from completely everting upon itself, or from everting beyond a particular percentage of eversion, for example. In some embodiments, the stop member 134 may be positioned to allow partial eversion of the bag 122. In some embodiments, the stop member 134 may be positioned to prevent substantially any eversion of the bag 122. The tethers 124 or tether bundle 130 may move distally through the lumen 118 until the stop member 134 abuts the proximal end 110 of the tube to prevent the tethers 124 or tether bundle from further moving distally through the lumen 118.

In some embodiments, the tethers 124 may be knotted together, or the tether bundle 130 may be knotted upon itself to provide the stop member 134 in the form of a knot. In some embodiments, the knot may have a diameter that is larger than the diameter of the lumen 118 of the tube 106. Accordingly, the tether bundle 130 may move distally within the lumen 118, and the distal portion of the tethers 124 may move distally (e.g., through the respective apertures 120) until the stop member 134 abuts the proximal end 110 of the tube 106.

Alternative forms of the stop member 134 are also possible. In some embodiments, the tether bundle 130 may be fused along the proximal end region 136 to form a single fiber, and a stop member such as a washer, or the like, may be crimped, clamped, adhesively attached, or otherwise attached to the proximal end region 136 of the tether bundle 130. In some embodiments, the stop member 134 may be provided as a bead (e.g., a polymer bead) that can be attached to the fused proximal end region 136 of the tether bundle 130. In accordance with some embodiments, the stop member 134 may have a width or a diameter that is larger than the diameter of the lumen 118 of the tube 106.

While the stop member 134 in FIGS. 1A, 1B, 1C, and 1D is located on the tether bundle 130 at a proximal end region 136 of the tether bundle 130, in some embodiments one or more stop members 134 can be located on the tether bundle 130 (or on individual tethers 124 or the tether bundle) within the lumen 118 of the tube (not shown), and can be sized larger than the apertures 120 to limit distal movement of the tethers 124. In some embodiments, each tether 124 of the one or more tethers includes such an alternative stop member 134, each of which may be individually sized larger than a corresponding aperture 120, but small enough so that the tethers 124 or tether bundle 130 may still be translated through the lumen 118 of the tube 106 (e.g., without becoming stuck in the lumen). The tethers 124 may move distally through the apertures 120 until the one or more alternative stop members 134 abut internal edges of the corresponding apertures 120 and prevent the tethers 124 from further moving distally through the corresponding apertures 120. Such alternative stop members 134 may be formed as a knot in the respective tether 124, in accordance with an embodiment, or may be one of the other types of stop members discussed above. In a general embodiment, the alternative stop members 134 may have a width or a diameter that is larger than the diameter of the apertures 120 within the tube 106.

Other types of travel limits of the tethers 124 are also possible. In accordance with an embodiment, the lumen 118 may include one or more tabs or protrusions that may limit travel in the distal direction of the tethers 124, tether bundle 130, or stop members on the tethers 124 or tether bundle 130. Additionally, in some embodiments, the filtration device 100 or 180 may include multiple stop members disposed at different positions along the tether bundle 130 or the individual tethers 124. In some embodiments, each of the multiple stop members may be sized to require a different amount of force to overcome a transition of the particular stop member beyond a particular feature (e.g., the proximal end 110, an aperture 120, or a tab or protrusion within the lumen 118 (not shown)) of the elongate member 102.

In some embodiments, the filtration device 100 may include one or more distal stop members (not shown) that are adapted to prevent the one or more tethers 124 from moving proximally beyond a particular position. The one or more distal stop members can be located on individual tethers 124, or in some cases on the transition regions 132, and can be sized larger than the apertures 120 to prevent proximal translation beyond the location of the apertures 120 in the tube 106. Such distal stop members may prevent inadvertent stretching or tearing of the bag 122 when the tethers 124 or tether bundle 130 is pulled taut by an operator, for example. The tethers 124 may move proximally through the apertures 120 until the distal stop members abut external edges of the corresponding apertures 120 and prevent the tethers 124 from further moving proximally through the corresponding apertures 120. In some embodiments, the tethers 124 may be knotted upon themselves to provide the distal stop members in the form of knots, or may be one of the other types of stop members discussed above. In a general embodiment, the distal stop members may have a width or a diameter that is larger than the diameter of the apertures 120 within the tube 106.

In some embodiments, the filtration device 100 or 180 may include one or more stop members that may be located at other positions along the length of the tether bundle 130 or the individual tethers 124. Similarly, the tube 106 may include one or more stop member engagement features designed to limit travel of the tether bundle 130 or individual tethers 124 at various locations along the tube 106. These stop members may allow for partial deployment of the filtration device 100 or 180, for example (e.g., may facilitate partial expansion of the bag 122).

The stop members 1354 discussed herein can be formed of one or more of a variety of biocompatible materials. In accordance with an embodiment, the stop member 134, alternative stop members, or the distal stop members may be formed of PTFE, ePTFE, silicone, an elastomeric fluoropolymer, stainless steel, or other appropriate materials. In some embodiments, the stop member 134 is substantially the same size as the outer diameter of the tube.

In some embodiments, the filtration device 100 or 180 can include one or more markers that allow the corresponding portion of the filtration device to be visualized during delivery and deployment, for example. In some embodiments, the markers may be radiopaque markers. For example, one or more radiopaque bands or markers may be disposed at particular positions along the length of the tethers 124 to allow for visualization of the position of the tethers. In some embodiments, one or more radiopaque bands or markers can be included on the bag 122, such as on the rim portion of the bag 122 or along the proximal edge of the bag 122, and may be used to identify the position of the mouth of the deployed filter, for example. In some embodiments, the radiopaque markers are gold bands. In some embodiments, one or more regions of the membranous member 104 may be imbibed with a radiopaque substance. In some embodiments, radiopaque dots may be disposed along the filtration surface of the bag 122. In some embodiments, the markers may be temporary markers whose visualization characteristics decay over time or in the presence of certain fluid components.

In some embodiments, the filtration device 100 or 180 may include a combination of one or more stop members and one or more markers. In some embodiments, a marker may be used instead of a stop. In some embodiments, the filtration device 100 or 180 may not include the stop member 134, and may instead include one or more markers that can be viewed to indicate when the device has assumed the deployed configuration (e.g., when substantial deployment of the filtration device has been achieved), or to indicate when the filtration device 100 or 180 has assumed the delivery configuration (e.g., for repositioning or retraction of the device).

In some embodiments, the bag 122 may include one or more struts (not shown) disposed, for example, along a portion of the filtration surface of the bag 122. In various embodiments, such struts could be disposed along the inner surface of the bag, or along the outer surface of the bag, or both. In accordance with an embodiment, the struts may be disposed near the distal end of the bag 122 and/or near the proximal end of the bag 122. In some embodiments, the struts may be disposed along a longitudinal length of the bag 122, and may take a variety of shapes (e.g., a helical shape, a sinusoidal shape, a zig-zag shape, a checkerboard shape, or others). In some embodiments, the struts may include a shape memory property that assists the bag 122 in achieving a prescribed shape when the filtration device 100 or 180 is allowed to deploy. Some embodiments do not include the one or more struts.

In embodiments of the filtration device that include struts, the struts may be made of Nitinol (NiTi), L605 steel, stainless steel, or other appropriate biocompatible material. In some embodiments, the struts may be attached to the inner surface or the outer surface of the bag 122 with an adhesive substance, such as FEP, or with any other appropriate adhesive substance.

In some embodiments, the filtration device 100 or 180 may be assembled by attaching the membranous member 104 to the tip 108 of the elongate member 102. In some embodiments, the distal end of the bag 122 can be fused (e.g., melted) to the distal end 116 of the tip 108. In some embodiments, the distal end of the bag 122 can be attached to the distal end 116 of the tip 108 using an adhesive substance, such as FEP, a biocompatible epoxy, or other adhesive substances known to one of skill in the art. In some embodiments, the distal end of the bag 122 can be attached to the distal end 116 of the tip 108 using conventional heat-treating techniques known to one of skill in the art. In some embodiments, the membranous member 104 may be precut and adapted to form the tethers 124 (as discussed above) prior to being attached to the tip 108. In other embodiments, the membranous member 104 may be cut and adapted to form the tethers 124 (as discussed above) after being attached to the tip 108.

Following formation of the tethers 124, the tethers 124 may be passed through the apertures 120 of the tube 106 of the elongate member 102. In some embodiments, the tether bundle 130 may be fused into a single fiber along the proximal end region 136 of the tether bundle 130 (e.g., where the tethers 124 exit the lumen 118 of the tube 106). The proximal end region 136 of the tether bundle 130 may subsequently be knotted upon itself to form the stop member 134. In some embodiments, one or more struts may be attached to the bag 122 prior to attaching the membranous member 104 to the tip 108. In some embodiments, the tethers 124 may be knotted upon themselves to form distal stops, as discussed above, prior to passing the tethers 124 through the apertures 120 within the tube 106. In some embodiments, other forms of distal stops may be attached to the tethers 124 before or after passing the tethers 124 through the apertures 120 within the tube 106. In some embodiments, one or more radiopaque markers may be added to the membranous member 104, either before or after coupling the membranous member 104 to the elongate member 102.

In some embodiments, the tethers 124 do not extend all the way through the lumen 118 of the tube 106. The tethers 124 may extend from the bag 122 through a corresponding aperture 120 of the tube, as described above, but within the lumen 118 of the tube each of the tethers 124 may be attached to a wire or other elongate member (not shown) that extends through lumen 118 and proximally beyond the proximal end 110 of the tube. In some embodiments, this wire or other elongate member can include a stop member 134 at a location proximal of the proximal end 110 of the tube. The wire or other elongate member to which the tethers 124 are attached may be manipulated by an operator. For example, the operator may apply a proximally directed force to the wire to pull the tethers 124 taut and collapse the bag 122 against the tip 108, in a similar manner as the operator would manipulate the tether bundle 130 or individual tethers as described above. Similarly, the operator may release tension on the wire, which may impart a slack to the tethers 124 and the bag 122, similar to releasing the tension on the tether bundle 130 or tethers 124 as described above. In some cases, the operator may apply a distally directed force to the wire to provide slack to the tethers 124 and the bag 122 to facilitate deployment of the device.

Figure 2A:
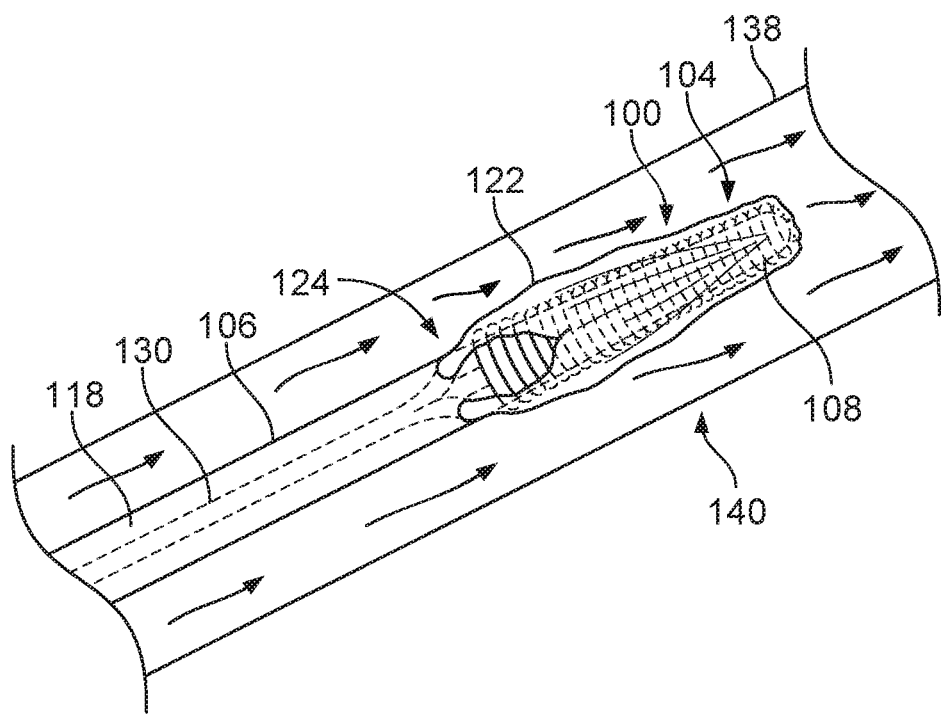
FIGS. 2A and 2B are perspective views of the embodiment of the filtration device of FIGS. 1A and 1B, shown in a conduit within a patient.
Figure 2B:
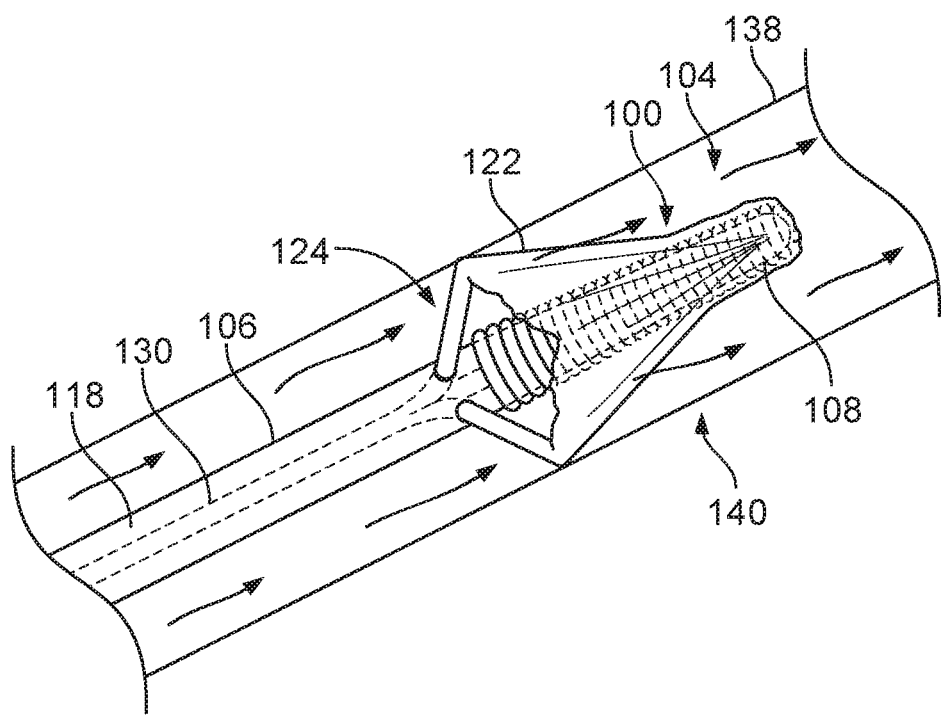

FIGS. 2A and 2B illustrate the filtration device 100 disposed in a conduit 138 within a patient. In some embodiments, the conduit 138 may be a blood vessel. Referring particularly to FIG. 2A, the tether bundle 130 of the filtration device 100 may be pulled taut proximally, as shown in FIG. 1A, causing the bag 122 to collapse against the outer surface of the tip 108 so that the filtration device 100 assumes the delivery configuration, as discussed above. In this manner, the low profile provided by the delivery configuration allows the filtration device 100 to be delivered to a delivery site 140 without using a catheter, such as a delivery catheter that may be used to constrain filter components (e.g., a frame) of alternative filtration devices. In alternative embodiments, however, the filtration device 100 may be used with a delivery catheter. In some embodiments, one or more distal stop members (not shown) that may be disposed on the tethers 124 may prevent the tether bundle 130 from being pulled proximally beyond a prescribed position.

In the delivery configuration, the filtration device 100 can be delivered to the delivery site 140 (e.g., a particular position along the length of the conduit 138) by advancing the filtration device 100 through the conduit 138. In some embodiments, the distal end of the filtration device 100 is advanced through the conduit 138 in the direction (see arrows in FIGS. 2A and 2B) of fluid flowing through the conduit 138, such that the bag 122 of the membranous member 104 can, when deployed, filter debris (e.g., embolic debris) carried by the fluid flowing through the conduit 138. In this manner, the debris can be prevented from flowing downstream of the delivery site 140.

Referring particularly to FIG. 2B, when the filtration device 100 is positioned at the delivery site 140, the tether bundle 130 as shown in FIG. 1B, may be released from its taut, proximal position, which may impart slack to the tether bundle 130 and the individual tethers 124. The slack in the tethers 124 may permit the proximal end of the bag 122 to have a looser fit against the elongate member 102, so that the fluid flowing in the conduit 138 may enter a mouth of the bag 122 and impart a force on an inner surface of the bag 122. The force of the fluid flowing through the conduit 138 may exert a force on the inner surface, or filtration surface, of the bag 122, and may cause the filtration surface of the bag to extend from the surface of the tip 108 of the elongate member 102. In some embodiments, the tether bundle 130 may move distally within the lumen 118 of the tube 106 until the stop member 134 abuts the proximal end 110 of the tube 106, as shown in FIG. 1B. In this manner, the filtration device 100 may be deployed, at least in part, by the force of the fluid flowing through the conduit 138. The deployment of the device may not rely on a frame or on a shape memory property, in accordance with an embodiment, as compared to expandable frames that underlie filters of some alternative filtration devices. Once deployed at the delivery site 140, the filtration device 100 may be operable to filter the debris carried by the fluid flowing through the conduit 138.

In some embodiments, the deployment of the bag 122 may be aided by an extension of struts disposed along the inner surface of the bag 122. In some embodiments, one or more radiopaque markers on the filtration device 100 may allow the operator to visualize a state of the filtration device 100 during delivery, deployment, or use of the filtration device 100.

Following a filtration period (e.g., following completion of an interventional vascular procedure), the filtration device 100 may be removed from the conduit 138. In some embodiments, the tether bundle 130 may be once again pulled taut and proximally, causing the bag 122 to be pulled tightly against the tip 108 of the elongate member, so that the filtration device 100 to again assumes the delivery configuration. In this manner, any debris collected within the bag 122 may be pushed against the surface of the tip 108 by the bag 122, and the mouth of the bag may be collapsed to prevent any debris from exiting the mouth of the bag. Depending on the amount of debris collected during the filtration period, bag 122 may bulge slightly from the surface of the tip 108 as compared to the delivery configuration pre-filtration. The filtration device 100 and the collected debris within the bag 122 may then be retracted proximally from the delivery site 140 and removed from the conduit 138 by withdrawing the elongate member 102 while maintaining the tension on the tether bundle 130.

Figure 3:
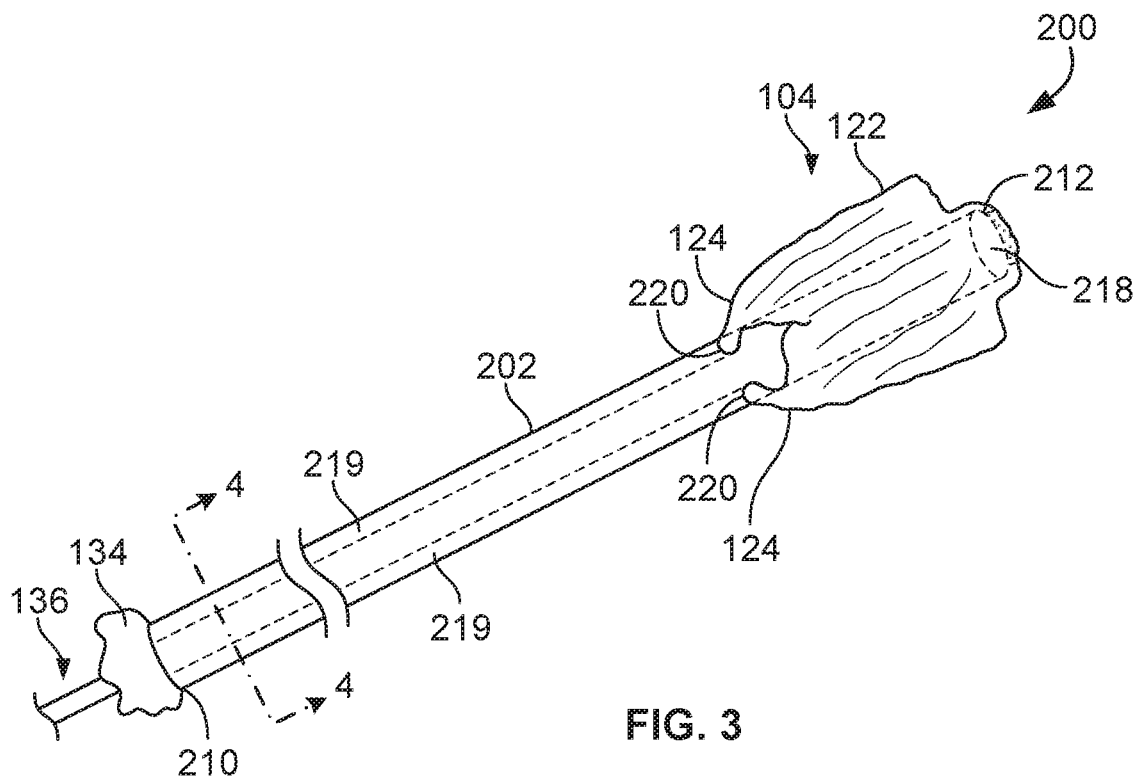
FIG. 3 is a perspective view of an embodiment of a filtration device.
Figure 4:
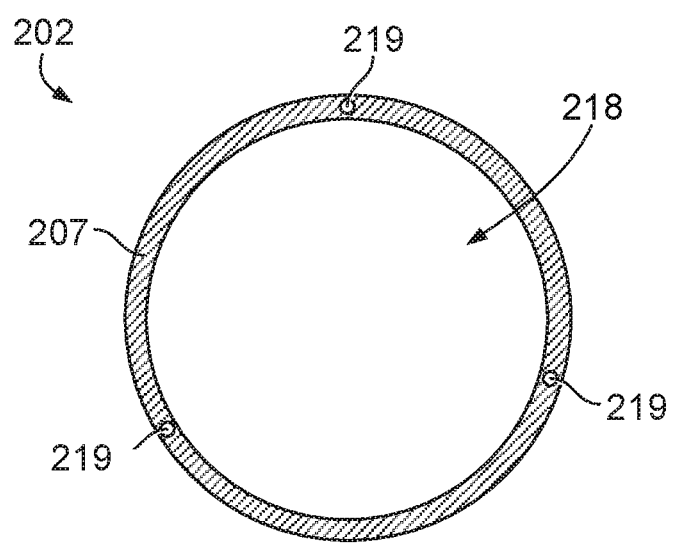
FIG. 4 is a cross-sectional view of a proximal end region of an elongate member of the filtration device of FIG. 3 at cutting plane 4-4.

In some embodiments, a filtration device may include an elongate member that guides tethers of a membranous member longitudinally through a channel in a wall of the elongate member. For example, FIG. 3 illustrates a perspective view of an embodiment of a filtration device 200 that includes the membranous member 104 of the filtration device 200 and an elongate member 202 that guides individual tethers 124 of the membranous member 104 through respective channels 219 in a wall 207, as shown in FIG. 4, of the elongate member 202. For simplicity, only two of the three channels 219 are shown in FIG. 3. The elongate member 202 is defined by a proximal end 210 and a distal end 212.

FIG. 4 illustrates a cross-sectional view of the elongate member 202. In some embodiments, the wall 207 of the elongate member 202 defines a lumen 218 through a center of the elongate member, and one or more channels 219 that extend longitudinally through and along a portion of the wall 207. In the depicted embodiment, three channels 219 are shown, but any appropriate number (one, two, four, five, six, seven, eight, or more) of channels 219 can be included. In some embodiments, the channels 219 may be spaced substantially equidistantly about a circumference of the elongate member 202, and may correspond to the spacing of the tethers 124 of the membranous member 104. In some embodiments, however, the channels 219 may be unequally spaced about the circumference of the elongate member 202. The channels 219 may be sized to allow passage of the tethers 124. In some embodiments, the elongate member 202 may have an outer diameter of about 0.020 inches to about 0.0150 inches and a wall thickness of about 0.003 inches to about 0.040 inches. In some embodiments the elongate member 202 has an outer diameter of up to about 0.300 inches. In some embodiments, a filtration device can include an elongate member and a membranous member having a different number (e.g., one, two, four, five, six, seven, eight, or more) of channels and corresponding tethers, respectively. Referring again to FIG. 3, in some embodiments, the channels 219 may extend from the proximal end 210 of the elongate member 202 to respective apertures 220 that extend from an outer surface of the wall 207 to the channels 219 within the wall 207 of the elongate member 202.

In some embodiments, the elongate member 202 may be a catheter (e.g., a microcatheter) that is adapted to be inserted through a vessel (e.g., a blood vessel). In a general embodiment, dimensions of the elongate member 202 may be selected according to a size of a particular conduit in which the filtration device 200 will be deployed. The elongate member 202 can be formed of nitinol (NiTi), stainless steel, L605 steel, a polymer material, or any other appropriate biocompatible material. In some embodiments, the elongate member 202 can be cut (e.g., laser cut) from a hypotube. The hypotube may be cut, for example, to include a guidewire-flex profile. In some embodiments, the apertures 220 may be laser cut into the sidewall of the elongate member 202. In some embodiments, the channels 219 can be formed in the wall 207 of the elongate member 202 using standard techniques known to those skilled in the art.

Still referring to FIG. 3, in some embodiments, the distal end of the bag 122 of the membranous member 104 is attached to the distal end 212 of the elongate member 202. The tethers 124 extend proximally from the bag 122 to the apertures 220 and through the channels 219 within the wall 207 of the elongate member 202. The proximal end region 136 of the tethers 124 may be knotted to form the stop member 134. In some embodiments, the tethers 124 may move distally within the channels 219 until the stop member 134 abuts the proximal end 210 of the elongate member 202 and prevents the tethers 124 and the bag 122 from moving any further distally. In some embodiments, the filtration device 200 may additionally or alternatively include other stopping members, such as any of the various stopping members discussed above herein.

In some embodiments, the filtration device 200 may be used while performing any of the interventional vascular procedures described above. In some embodiments, one or more adjunct, therapeutic, or treatment devices may be passed through a lumen (e.g., lumen 218) of the elongate member 202 during use of the filtration device 200.

Figure 5:
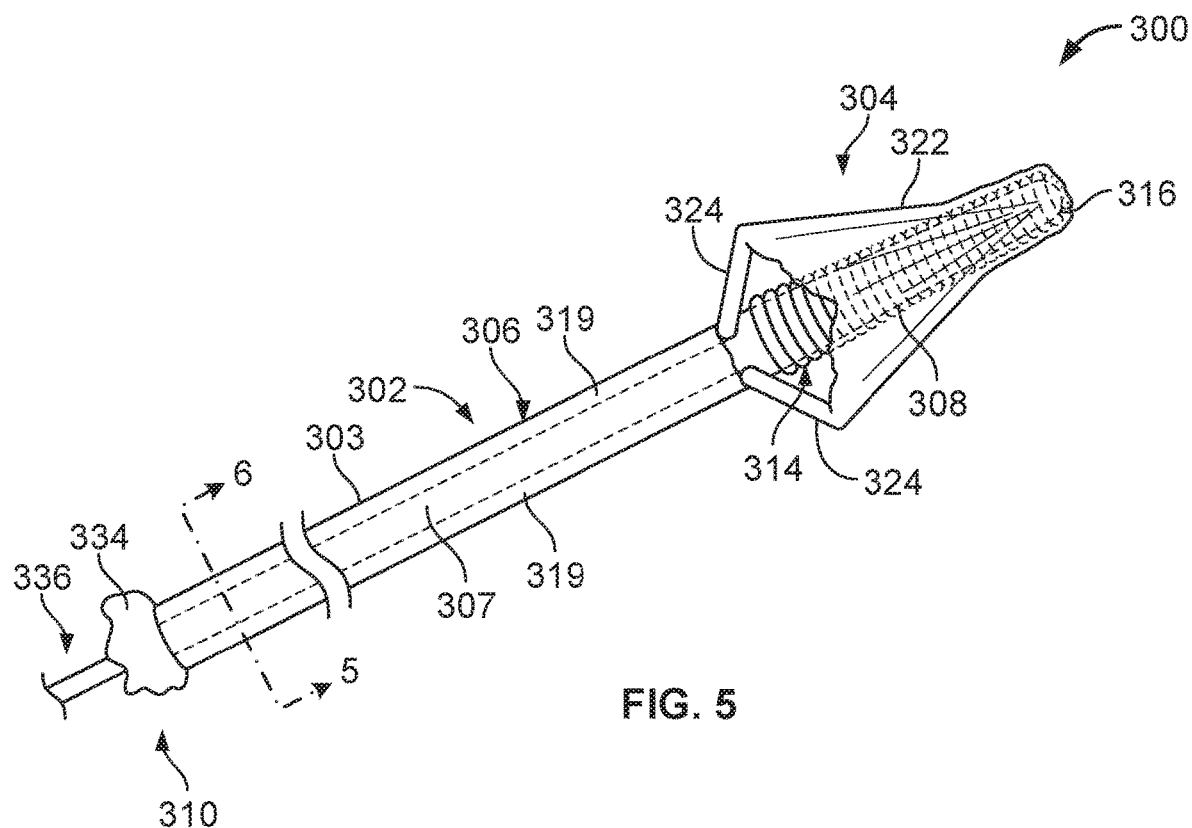
FIG. 5 is a perspective view of another embodiment of a filtration device.

In some embodiments, a filtration device may include an elongate member that guides one or more portions of the membranous member along an outer edge region of the elongate member. For example, FIG. 5 illustrates a perspective view of an embodiment of a filtration device 300 that includes a membranous member 304, an elongate member 302 that guides tethers 324 of the membranous member 304 along one or more outer edge regions of the elongate member 302, and a wrapping 303 that surrounds the elongate member 302. The membranous member 304 is substantially similar in construction and function to the membranous member 104 of the filtration devices 100, 180, 200, with the exception that the membranous member 304 includes two tethers 324 instead of three tethers. The elongate member 302 includes a shaft 306 and a tip 308 that extends distally from the shaft 306 to form the distal end region of the elongate member 302. The shaft 306 includes a proximal end 310, and the tip includes a distal end 316. In this embodiment, a coil 314 is included, but in some embodiments the coil 314 is not included.

Figure 6:
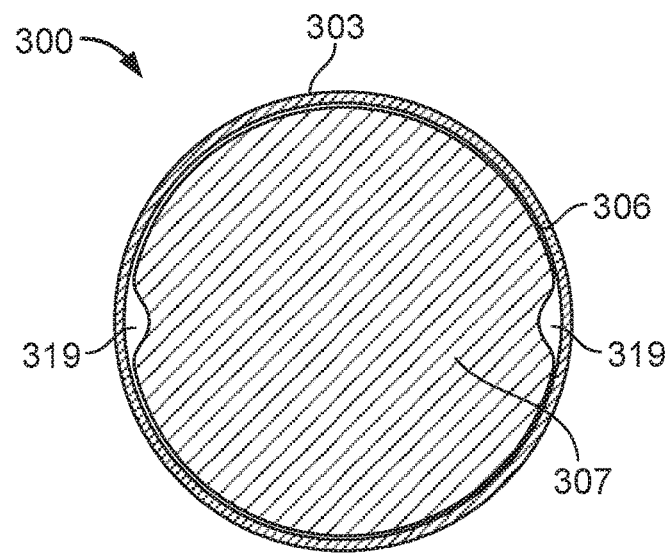
FIG. 6 is a cross-sectional view of a proximal end region of the filtration device of FIG. 5 at cutting plane 6-6.

FIG. 6 illustrates a cross-sectional view of a proximal end region of the filtration device 300 (facing proximally). In some embodiments, the shaft 306 has a solid core 307 and defines two opposing channels 319 that extend into the core 307 from an outer surface of the shaft 306. In the embodiment of the filtration device 300 of FIGS. 6 and 7, the channels 319 have a rounded cross-sectional shape. However, in some embodiments, a filtration device may include an elongate member that has channels that have a different cross-sectional shape (e.g., a rectangular shape). The shaft 306 may be a guidewire, and the channels 319 may be grooves that are ground along the longitudinal length of the guidewire. In some embodiments, the guidewire is a stainless steel guidewire. The wrapping 303 can be a film that is wrapped over the shaft 306, so that the wrapping and the grooves form the channels 319. In some embodiments, the wrapping 303 may be wrapped around and secured to the outer surface of the shaft 306 of the elongate member 302.

In some embodiments, the grooves may have a depth and a width that allow the channels 319 to receive the tethers 324 and permit translation of the tethers 324 within the channels. In some embodiments, a filtration device can include an elongate member and a membranous member having a different number (e.g., one, three, four, five, six, seven, eight, or more) of channels and corresponding tethers.

In some embodiments, the elongate member 302 may be a guide wire that is adapted to be inserted through a blood vessel. In a general embodiment, dimensions of the elongate member 302 may be selected according to a size of a particular conduit in which the filtration device 300 will be deployed. For example, the dimensions of the elongate member 302 may be selected according to the size of a 0.010", 0.014", or 0.035" guide wire, as will be known to one of skill in the art.

Referring again to FIG. 5, in some embodiments, the tip 308 is substantially similar in construction and function to the tip 108 of the filtration device 100. In some embodiments, the distal end of a bag 322 of the membranous member 304 is attached to the distal end 312 of the tip 308. The tethers 324 extend proximally from the bag 322 along respective channels 319 and past the proximal end 310 of the shaft 306. A proximal end region 336 of the tethers 324 may be knotted to form a stop member 334. Other types of stop members may also be used. In some embodiments, as the tethers 324 move distally within the channels 319, the stop member 334 may abut the proximal end 310 of the shaft 306, and prevent the tethers 324 and bag 322 from further distal movement. In some embodiments, the filtration device 300 may additionally or alternatively include other stopping members.

In some embodiments, the wrapping 303 may include slits or openings (not shown) that are disposed along a distal end region of the wrapping 303 and that allow passage of the tethers 324 into the channels 319. In some embodiments, the wrapping includes one or more skives (not shown), that allow passage of the tethers 324 into the channels 319. In some embodiments, the tethers 324 may enter channels 319 at a distal end of the wrapping 303. The wrapping 303 can be formed of one or more of a variety of biocompatible materials, such as PTFE, ePTFE, polyester, polyimide, PEBAX (polyether block amide), nylon, or PET. In some embodiments, the wrapping 303 may be secured to the outer surface of the elongate member 302 by an adhesive, such as FEP or another appropriate adhesive, as described above.

In some embodiments, the filtration device 300 may be collapsed and deployed in the same manner as that described with reference to the filtration devices 100 or 180. In some embodiments, the configuration of the filtration device 300 allows the filtration device 300 to be delivered to a delivery site without using a catheter. However, in some embodiments, the filtration device 300 may be delivered within a catheter. In some embodiments, the filtration device 300 may be used while performing any of the interventional vascular procedures described above.

Figure 7:
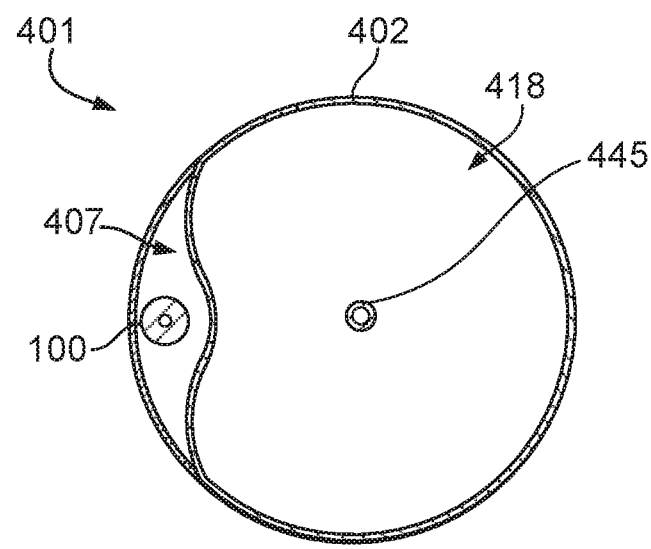
FIG. 7 is a cross-sectional view of a distal end of an embodiment of a treatment kit shown in FIG. 8 at cutting plane 7-7 that includes the filtration device of FIGS. 1A and 1B.

In some embodiments, the filtration device 100 may be included in a treatment kit that allows for simultaneous advancement of the filtration device and a treatment tool to a delivery site. For example, FIG. 7 illustrates a cross-sectional view of a distal end of an embodiment of a treatment kit 401, shown in FIG. 8, which may be used to perform an interventional vascular procedure, such as any of the procedures described above herein. The treatment kit 401 includes an elongate member 402, which may be a microcatheter in some embodiments, the filtration device 100 (or any of the other filtration devices discussed herein), and a treatment tool 403. The elongate member 402 is defined by a proximal end (not shown) and a distal end 412. shown in FIG. 8. The elongate member 402 defines a wall lumen 407, sized for passage of the filtration device 100, and a working lumen 418, sized for passage of the treatment tool 403. In some embodiments, the working lumen 418 may have a width of about 0.027", and the elongate member 402 may have a size similar to or equivalent to a 0.054" catheter.

In some embodiments, the configuration of the elongate member 402 can allow simultaneous advancement of the filtration device 100 and the treatment tool 403 within a blood vessel or other conduit. In some embodiments, the treatment tool 403 may be a thrombectomy device, an angioplasty balloon, a stent, an atherectomy device, a cutting balloon, a suction device, a drug delivery device, or another type of treatment device, and may be attached to a wire. In some embodiments, distal ends of the filtration device 100 and the treatment tool 403 may be advanced distally out of the wall lumen 407 and the working lumen 418, respectively. In accordance with an embodiment, the filtration device 100 may be advanced by advancing elongate member 102 of the filtration device 100 through the wall lumen 407, and then distally of the distal end 412 of the elongate member 402. The treatment tool 403 may attached to a wire 445, which may be advanced through the working lumen 418 and then distally of the distal end 412 of the elongate member 402. In some embodiments, either or both maximum distances by which the filtration device 100 and the treatment tool 403 may be extended from the distal end 412 of the elongate member 402 may be fixed or adjustable.

Figure 8:
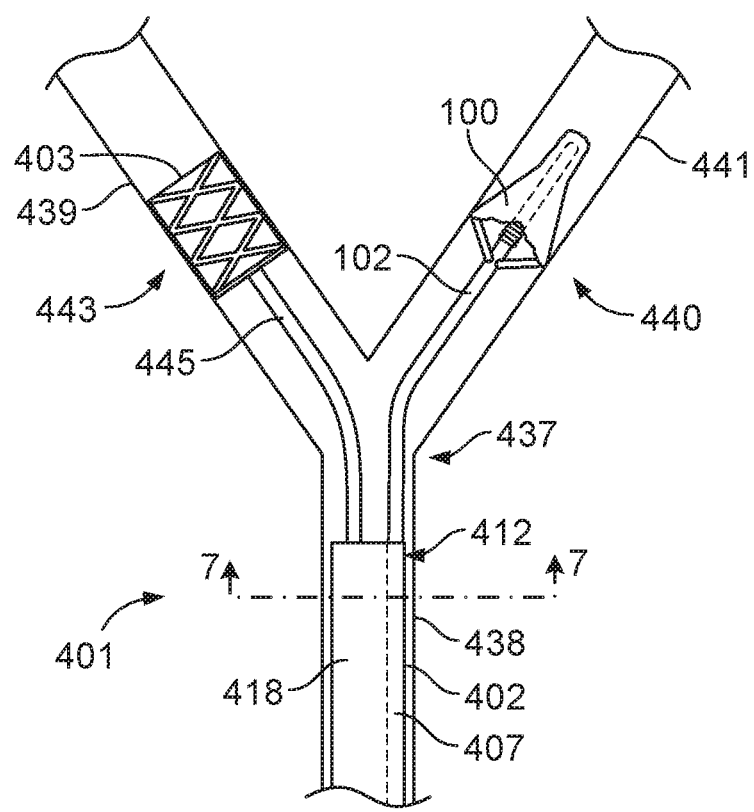
FIG. 8 is a top view of the treatment kit of FIG. 7 shown in a conduit within a patient.

FIG. 8 illustrates the treatment kit 401 within a conduit 438 (e.g., a blood vessel) of a patient. In some embodiments, the elongate member 402 of the treatment kit 401 may be delivered to a bifurcation point 437 within the conduit 438. In some embodiments, from the bifurcation point 437, the conduit 438 may branch distally into a first conduit 439, in which a treatment procedure (e.g., a thrombectomy procedure) may be performed, and a second conduit 441, in which distal filtration may be implemented. In accordance with an embodiment, the first conduit 439 may contain a thrombus that has been targeted for treatment. In some embodiments, the filtration device 100 may be advanced distally to a delivery site 440 within the second conduit 441, and the filtration device 100 may then be deployed to implement filtration, in a manner as discussed above with reference to FIGS. 1B and 2B. Once distal filtration has been implemented in the second conduit 441, the treatment tool 403 may be advanced distally to a treatment site 443 within the first conduit 439, where the treatment tool 403 may be operated to perform the treatment procedure at the treatment site 443 using standard techniques known to one of skill in the art.

By filtering a side branch of a bifurcated vessel, as shown in FIG. 8, emboli that may be lost to side branches during clot retrieval may be prevented from passing further into the patient's vasculature, for example. In some embodiments, the filtration device 100 could alternatively be deployed in the first conduit, distal of the treatment site 443.

In some embodiments, the treatment kit can include a second wall lumen 407 (e.g., on the opposing side of the elongate member 402), and a second filtration device that can be advanced through the second wall lumen 407. A first filtration device can be delivered and deployed in the first conduit 439, distal of the treatment site 443, to provide distal filtration within the first conduit 439, and a second filtration device can be delivered and deployed in the second conduit 441, to provide filtration of the side branch. The treatment tool may then be advanced to the treatment site 443 within the first conduit 439, where the treatment tool 403 may be operated to perform the treatment procedure.

Following completion of the procedure, the treatment tool 403 may be retracted into the working lumen 418, as by pulling on the wire 445. The one or more filtration devices 100 may remain deployed during this process, so that any debris that may be liberated from the tool 403 as it is being loaded into the elongate member 402 may be captured by the one or more filtration devices. In some embodiments, the one or more filtration devices 100 may be collapsed to the delivery configuration and retracted into the wall lumen 407, carrying any debris (e.g., embolic debris) collected during the filtration period. In some embodiments, an aspiration catheter (e.g., delivered through working lumen 418) may be used to aspirate debris from the filtration device before withdrawing the filtration device.

In some embodiments, after the filtration device 100 and the treatment tool 403 have been retracted to within the wall lumen 407 and the working lumen 418, respectively, the treatment kit 401 may be retracted proximally from the bifurcation point 437 and removed from the conduit 438. In some embodiments, the filtration device 100 may be retracted into the wall lumen 407 prior to the treatment tool 403 being retracted into the working lumen 418. In some embodiments, either or both of the treatment tool 403 and the filtration device 100 may be removed from (e.g., proximally withdrawn from) the elongate member 402 prior to the elongate member 402 being removed from the conduit 438.

Figure 9A:
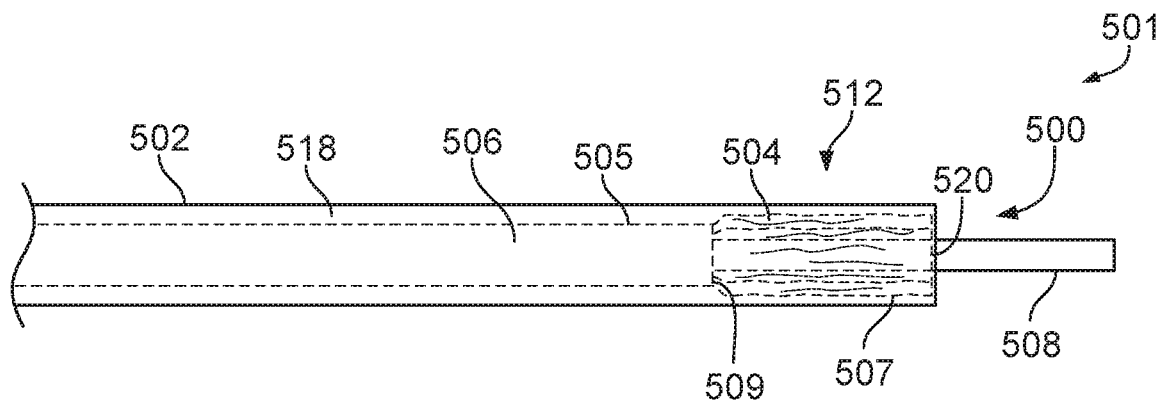
FIGS. 9A and 9B are side views of another embodiment of a treatment kit.
Figure 9B:
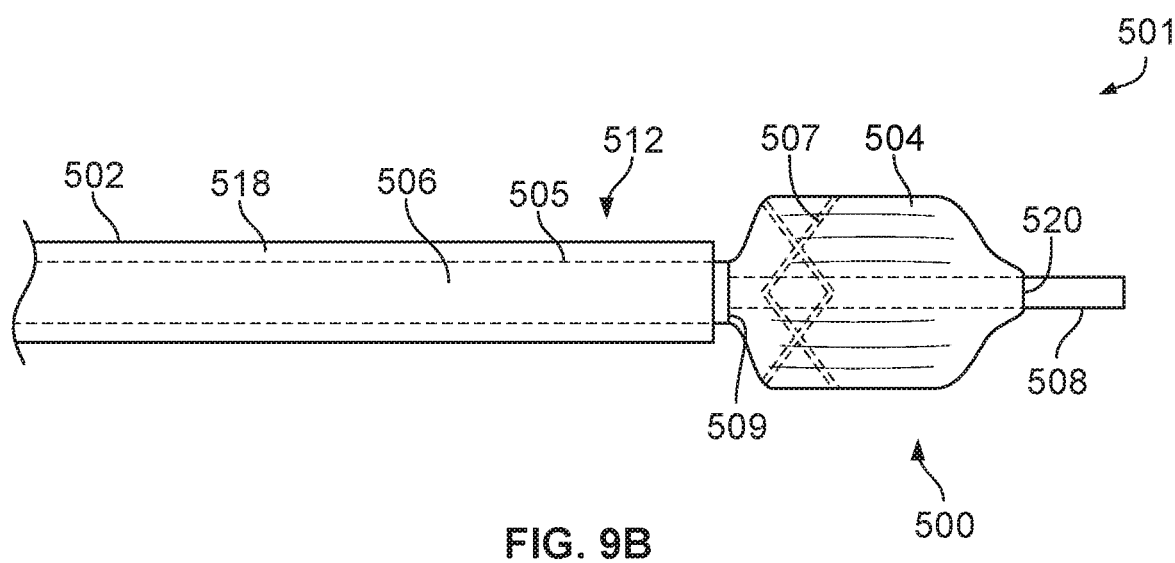

In some embodiments, a treatment kit may include a filtration device that is attached to an elongate member. In accordance with an embodiment, FIGS. 9A and 9B illustrate a distal end of an embodiment of a treatment kit 501, shown for delivery and deployed configurations, respectively, of a filtration device 500 that can be deployed in a conduit within a patient. The treatment kit 501 includes an elongate member 502, the filtration device 500, and a deployment device 505. The treatment kit 501 may further optionally include a treatment tool (not shown) that is sized to pass through a lumen of the elongate member 502.

The elongate member 502 is defined by a proximal end (not shown) and a distal end region 512. The elongate member 502 defines a lumen 518 sized to allow passage of the filtration device 500, the deployment device 505, and, optionally, the treatment tool. In some embodiments, the elongate member 502 may be a catheter (e.g., a microcatheter).

In some embodiments, the filtration device 500 includes a membranous member 504, one or more struts 507 that underlie a portion of the membranous member 504, and one or more tethers (not shown) that extend proximally from the membranous member 504. In some embodiments, the membranous member 504 is adapted to allow passage of certain blood components (e.g., blood cells and platelets), but to prevent passage of debris (e.g., embolic debris) carried by blood flowing through the membranous member 504. In some embodiments, the membranous member 504 may include an opening 520 through which a portion of the deployment device 505 may pass, as will be discussed in more detail below.

In some embodiments, the one or more tethers may be coupled to the elongate member 502 and may prevent the filtration device 500 from separating from the elongate member 502. In accordance with an embodiment, the one or more tethers may extend longitudinally through a wall of the elongate member 502. In some embodiments, the one or more tethers may extend through the lumen 518 of the elongate member 502. In some embodiments, the one or more tethers may be pulled proximally taut by an operator to cause the membranous member 504 and the one or more struts 507 to collapse towards an outer surface of the deployment device 505, see FIG. 9A, such that the filtration device 500 may be passed proximally through the lumen 518 of the elongate member 502. In some embodiments, the one or more struts 507 may have a shape memory property that allow the one or more struts 507 to expand to a prescribed shape when the frame is unconstrained. The one or more struts 507 can be formed of one or more of a variety of biocompatible materials, such as NiTi, stainless steel, L605 steel, a polymer material, or any other appropriate biocompatible material.

In some embodiments, the filtration device 500 may assume various configurations. In accordance with an embodiment, when the distal end of the filtration device 500 is disposed and constrained within the lumen 518 of the elongate member 502, the filtration device 500 may assume a delivery configuration, see FIG. 9A. In some embodiments, when the membranous member 504 and the one or more struts 507 are extended past the distal end region 512 of the elongate member 502, the one or more struts 507 may expand such that the filtration device 500 assumes a deployed configuration, see FIG. 9B.

In some embodiments, the deployment device 505 may include a shaft 506 and a tip 508 that extends distally from the shaft 506. In some embodiments, the shaft 506 forms a seat 509 that is configured to contact a proximal edge of the one or more struts 507. The filtration device 500 may be moved distally within the lumen 518 of the elongate member 502 by moving the deployment device 505 distally.

In some embodiments, the tip 508 is sized to pass through the opening 520 of the membranous member 504 and may serve to position the one or more struts 507 (e.g., to centrally align the one or more struts 507 with a central axis of the deployment device 505) when the one or more struts 507 expand, see FIG. 9B. In some embodiments, the tip 508 may have a diameter that is smaller than the diameter of the shaft 506. In some embodiments, the tip 508 may extend past the distal end region 512 of the elongate member 502 when the filtration device 500 assumes the delivery configuration, see FIG. 9A. In some embodiments, the tip 508 may be shapeable (e.g., bendable), such that the tip 508 can be formed to a shape that can aid in navigation of the treatment kit 501 within a conduit. In some embodiments, the deployment device 505 may be a guide wire. In some embodiments, the deployment device 505 may be a stepped guide wire. The deployment device 505 may be made of one or more biocompatible materials, such as NiTi, stainless steel, L605 steel, a polymer material, or any other appropriate biocompatible material.

Figure 10:
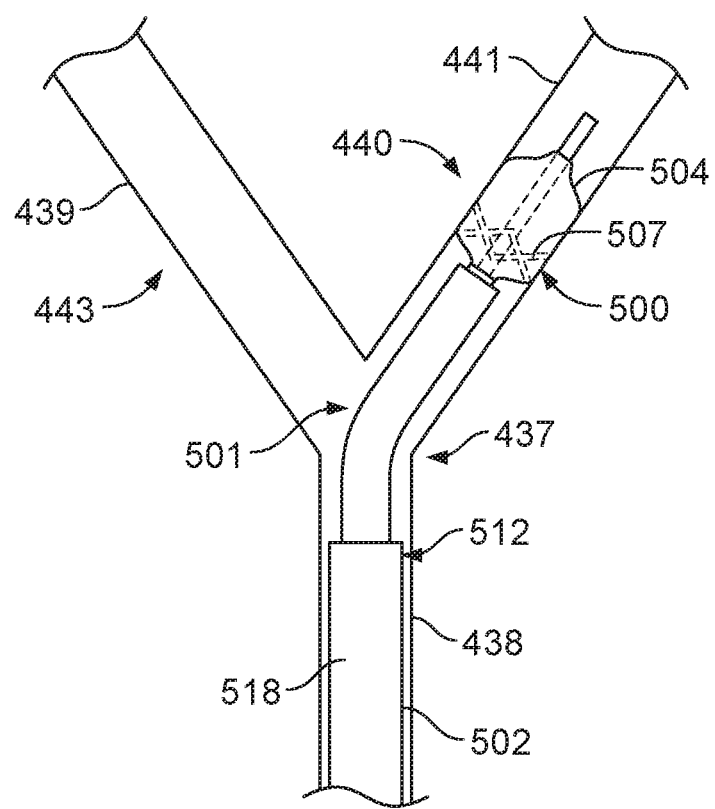
FIG. 10 is a top view of the treatment kit of FIGS. 9A and 9B shown in a conduit within a patient.

FIG. 10 illustrates the treatment kit 501 within the conduit 438 of FIG. 8. In some embodiments, the elongate member 502 of the treatment kit 501, carrying the filtration device 500 in the delivery configuration, may be delivered to the bifurcation point 437. In some embodiments, the deployment device 505 may be moved distally to advance the filtration device 500 distally to the delivery site 440 within the second conduit 441. Upon exiting the lumen 518 of the elongate member 502, the one or more struts 507 and the membranous member 504 may expand such that the filtration device 500 assumes the deployed configuration to implement distal filtration.

Several characteristics and advantages have been set forth in the preceding description, including various alternatives together with details of the structure and function of the devices and/or methods. The disclosure is intended as illustrative only, and as such is not intended to be exhaustive. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein. All references, publications, and patents referred to herein, including the figures and drawings included therewith, are incorporated by reference in their entirety.

What is claimed is:

1. A method of vascular filtration, comprising: advancing a vascular filtration device to a deployment site within a blood vessel, the vascular filtration device including an elongate member and an unsupported bag portion positioned along a distal portion of the elongate member and plurality of elongate extensions attached directly to the bag portion and extending to a proximal end of the elongate member, the vascular filtration device being advanced to the deployment site with the bag portion collapsed against the elongate member with the plurality of elongate extensions secured against translation relative to the elongate member; and releasing the plurality of elongate extensions such that the plurality of elongate extensions are free to translate relative to the elongate member, wherein blood flow through the blood vessel causes the bag portion to expand radially away from the elongate member, wherein the plurality of elongate extensions are spaced generally equidistantly about a perimeter of the bag portion.

2. The method of claim 1, wherein expansion of the bag portion radially away from the elongate member does not require use of an expansion aid.

3. The method of claim 1, wherein the bag portion is radially unsupported.

4. The method of claim 1, wherein the plurality of elongate extensions translate relative to the elongate member as the bag portion expands radially away from the elongate member.

5. The method of claim 1, further comprising applying a proximally-directed force to the plurality of elongate extensions of the bag portion to cause the bag portion to radially collapse against the elongate member, the proximally-directed force being applied after the vascular filtration device has been advanced to the deployment site and the elongate extensions have been released such that the bag portion has expanded radially away from the elongate member.

6. The method of claim 1, further comprising applying a proximally-directed force to the plurality of elongate extensions of the bag portion-during advancement of the vascular filtration device to the deployment site such that the bag portion is maintained against the elongate member.

7. The method of claim 1, wherein the bag portion consists of a porous polymeric material.

8. The method of claim 7, wherein the polymeric material includes expanded polytetrafluoroethylene.

9. The method of claim 1, wherein the plurality of elongate extensions and the bag portion are formed from a single sheet of material.

10. The method of claim 1, wherein the plurality of elongate extensions extend from a proximal portion of the bag portion.

11. The method of claim 1, wherein the vascular filtration device further includes a stop member adapted to limit an amount of distal translation of one or more of the plurality of elongate extensions within a limited range of movement, and wherein upon releasing the plurality of elongate extensions, the plurality of elongate extensions are free to translate distally relative to the elongate member within the limited range of movement.

12. The method of claim 1, wherein the vascular filtration device is adapted to occlude the vessel.

13. The method of claim 1, further comprising advancing a treatment device through a lumen of the blood vessel to a location upstream of the vascular filtration device, and using the treatment device to perform an interventional vascular procedure.

14. The method of claim 13, wherein the treatment device is a thrombectomy device and the interventional vascular procedure is a thrombectomy procedure.

15. The method of claim 13, wherein the treatment device is an atherectomy device and the interventional vascular procedure is an atherectomy procedure.

16. The method of claim 13, wherein the treatment device is a stent and the interventional vascular procedure is a stenting procedure.

17. The method of claim 13, wherein the treatment device is an angioplasty balloon and the interventional vascular procedure is an angioplasty procedure.

18. The method of claim 13, wherein the vascular filtration device and the treatment device are each located within the blood vessel.

19. The method of claim 1, wherein the blood vessel includes first and second branch vessels, and wherein the vascular filtration device is deployed in the second branch vessel, the method further comprising advancing a treatment device through a lumen of the blood vessel to a location in the first branch vessel and using the treatment device to perform an interventional vascular procedure.

20. The method of claim 1, further comprising aspirating debris collected by the vascular filtration device from the bag portion.

21. The method of claim 1, wherein the blood flow comprises injected fluid.

22. The method of claim 1, wherein the bag portion comprises a micro-porous material.

23. The method of claim 1, wherein the bag portion comprises a non-porous material.

24. The method of claim 1, wherein the vascular filtration device does not include a frame or support structure that has a shape memory property.

* * * * *